United States Patent
Fan et al.

(10) Patent No.: US 10,925,510 B2
(45) Date of Patent: Feb. 23, 2021

(54) CHARACTERIZATION OF RESPIRATORY MOTION IN THE ABDOMEN USING A 4D MRI TECHNIQUE WITH 3D RADIAL SAMPLING AND RESPIRATORY SELF-GATING

(71) Applicant: Cedars-Sinai Medical Center, Los Angeles, CA (US)

(72) Inventors: Zhaoyang Fan, Hacienda Heights, CA (US); Jianing Pang, Los Angeles, CA (US); Zixin Deng, Los Angeles, CA (US); Debiao Li, Pasadena, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1252 days.

(21) Appl. No.: 14/707,647

(22) Filed: May 8, 2015

(65) Prior Publication Data
US 2016/0324500 A1 Nov. 10, 2016

(51) Int. Cl.
| | | |
|---|---|---|
| *A61B 5/055* | (2006.01) | |
| *A61B 5/00* | (2006.01) | |
| *G01R 33/567* | (2006.01) | |
| *G01R 33/561* | (2006.01) | |
| *A61B 5/113* | (2006.01) | |
| *G01R 33/565* | (2006.01) | |
| *G01R 33/48* | (2006.01) | |

(52) U.S. Cl.
CPC ............ *A61B 5/055* (2013.01); *A61B 5/7207* (2013.01); *A61B 5/7257* (2013.01); *G01R 33/5676* (2013.01); *A61B 5/113* (2013.01); *G01R 33/4826* (2013.01); *G01R 33/5611* (2013.01); *G01R 33/56509* (2013.01)

(58) Field of Classification Search
CPC ..... A61B 5/055; A61B 5/7207; A61B 5/7257; A61B 5/113; G01R 33/5676; G01R 33/5611; G01R 33/56509; G01R 33/4826
See application file for complete search history.

(56) References Cited

U.S. PATENT DOCUMENTS

| | | | | |
|---|---|---|---|---|
| 5,041,789 A | * | 8/1991 | Keller | G01R 33/28 324/318 |
| 5,433,717 A | * | 7/1995 | Rubinsky | A61B 18/02 600/411 |
| 5,902,310 A | * | 5/1999 | Foerster | A61B 17/0644 606/142 |

(Continued)

OTHER PUBLICATIONS

Buerger et al., Nonrigid Motion Modeling of the Liver From 3-D Undersampled Self-Gated Golden-Radial Phase Encoded MRI, 2012, IEEE Trans. Med. Imaging, vol. 31, pp. 805-815 (Year: 2012).*

(Continued)

*Primary Examiner* — Keith M Raymond
*Assistant Examiner* — Patrick M Mehl
(74) *Attorney, Agent, or Firm* — Nixon Peabody LLP

(57) ABSTRACT

Magnetic resonance imaging utilizing a continuous spoiled gradient echo sequence with 3D radial trajectory and 1D self-gating for respiratory motion detection can be used to characterize respirator motion in the abdomen. The resulting image data is acquired and is retrospectively sorted into different respiratory phases based on their temporal locations within a respiratory cycle, and each phase is reconstructed via a self-calibrating conjugate gradient sensitivity encoding (CG-SENSE) program.

16 Claims, 13 Drawing Sheets

(56) References Cited

U.S. PATENT DOCUMENTS

| | | | | |
|---|---|---|---|---|
| 2009/0105582 | A1* | 4/2009 | Dougherty | A61B 5/055 600/420 |
| 2010/0268096 | A1* | 10/2010 | Berka | A61B 5/02433 600/485 |
| 2014/0070803 | A1* | 3/2014 | Jin | G01R 33/5605 324/309 |
| 2015/0374237 | A1* | 12/2015 | Hu | A61B 5/055 600/413 |

OTHER PUBLICATIONS

Odille et al., Model-Based Reconstruction for Cardiac Cine MRI Without ECG or Breath Holding, 2010, Magnetic Resonance in Medicine, pp. 1247-1257 (Year: 2010).*

Why 3 Tesla MRI?, Jan. 5, 2008, 3T Imaging and GK Medical Management, p. 1 (Year: 2008).*

Prieto et al., 3-D undersampled golden-radial phase encoding for DCE-MRA using inherently regularized iterative SENSE, 2010, Magnetic Resonance in Medicine, vol. 64, No. 2, pp. 514-526 (Year: 2010).*

Buerger et al. 2012, IEEE Trans. Med. Imaging 31:805-815 (Year: 2012).*

Prieto et al. 2010, Mag. Reson. in Med. 64:514-526 (Year: 2010).*

Coppo et al. 2015 Mag. Reson. in Med. 74:1306-1316 (Year: 2015).*

Stehning et al. 2005 Mag. Reson. In Med. 54:476-480 (Year: 2005).*

Feng et al. 2015 IEEE 12th International Symposium on Biomedical Imaging p. 889-892 (Year: 2015).*

Lin et al. 2008 Mag. Reson. in Med. 60:1135-1146 (Year: 2008).*

Lai et al. 2008 J. Mag. Reson. Imag. 28:612-620 (Year: 2008).*

Lazaro et al. 2013 Med. Biol. Eng. Comput. 51:233-242 (Year: 2013).*

Bieri et al. 2005 MRM 54:129-137 IDS (Year: 2005).*

Ingle 2014 PhD. Thesis Stanford University 156 pages (Year: 2014).*

Blackall, J.M. et al., MRI-based measurements of respiratory motion variability and assessment of imaging strategies for radiotherapy planning, Phys. Med. Biol., 2006, 51:4147-4169.

Buerger, C. et al., Nonrigid motion modeling of the liver from 3-D undersampled self-gated golden-radial phase encoded MRI, IEEE Trans. Med. Imaging, 2012, 31(3):805-815.

Cai, J. et al., Four-dimensional magnetic resonance imaging (4D-MRI) using image-based respiratory surrogate: A feasibility study, Medical Physics, 2011, 38(12):6384-6394.

Dinkel, J. et al., 4D-MRI analysis of lung tumor motion in patients with hemidiaphragmatic paralysis, Radiotherapy and Oncology, 2009, 91:449-454.

Hu, Y. et al., Respiratory amplitude guided 4D magnetic resonance imaging, Int. J. Radiation Oncololgy Biology Physics, 2013, 86(1):198-204.

Levitt, M.H., Composite pulses, Progress in N M R Spectroscopy, 1986, 18:61-122.

Plathow, C. et al., Monitoring of lung motion in patients with malignant pleural mesothelioma using two-dimensional and three-dimensional dynamic magnetic resonance imaging: Comparison with spirometry, Investigative Radiology, 2006, 41(5):443-448.

Prieto, C. et al., 3D undersampled golden radial phase encoding for DCE MRA using inherently regularized iterative SENSE, Magnetic Resonance in Medicine, 2010, 64:514-526.

Tokuda, J. et al., Adaptive 4D MR imaging using navigator based respiratory signal for MRI guided therapy, Magnetic Resonance in Medicine, 2008, 59:1051-1061.

Tryggestad, E. et al., Respiration based sorting of dynamic MRI to derive representative 4D MRI for radiotherapy planning, Medical Physics, 2013, 40(5):(051909)1-12.

Von Siebenthal, M. et al., 4D MR imaging of respiratory organ motion and its variability, Physics in Medicine and Biology, 2007, 52:1547-1564.

Von Siebenthal, M. et al., 4D MR imaging using internal respiratory gating, MICCAI, 2005, 3750:336-343.

* cited by examiner

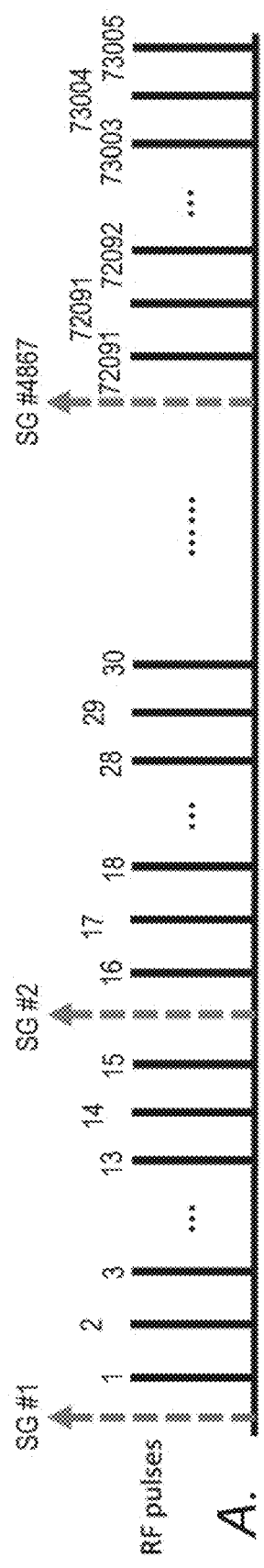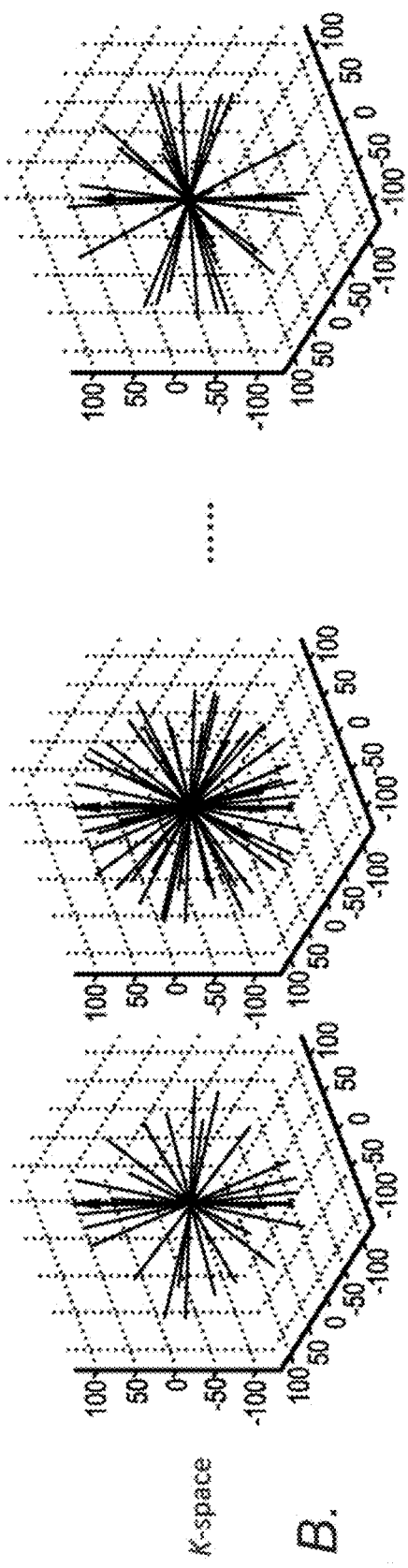
FIG. 2

FIG. 3A
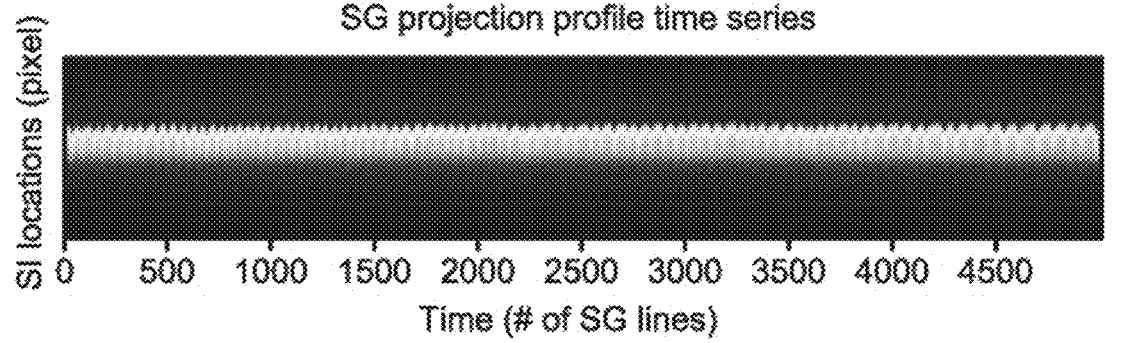
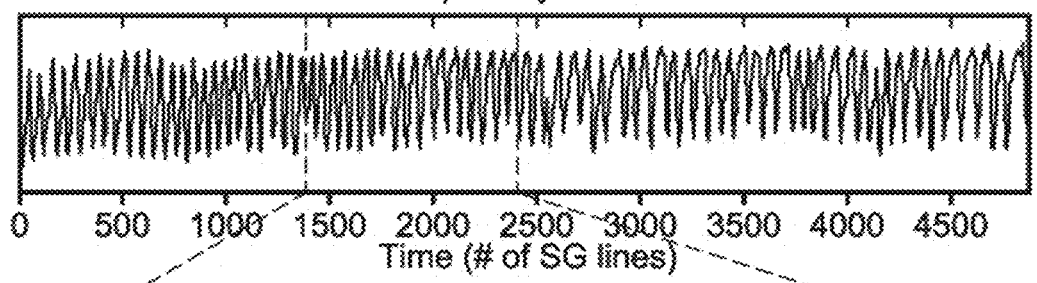
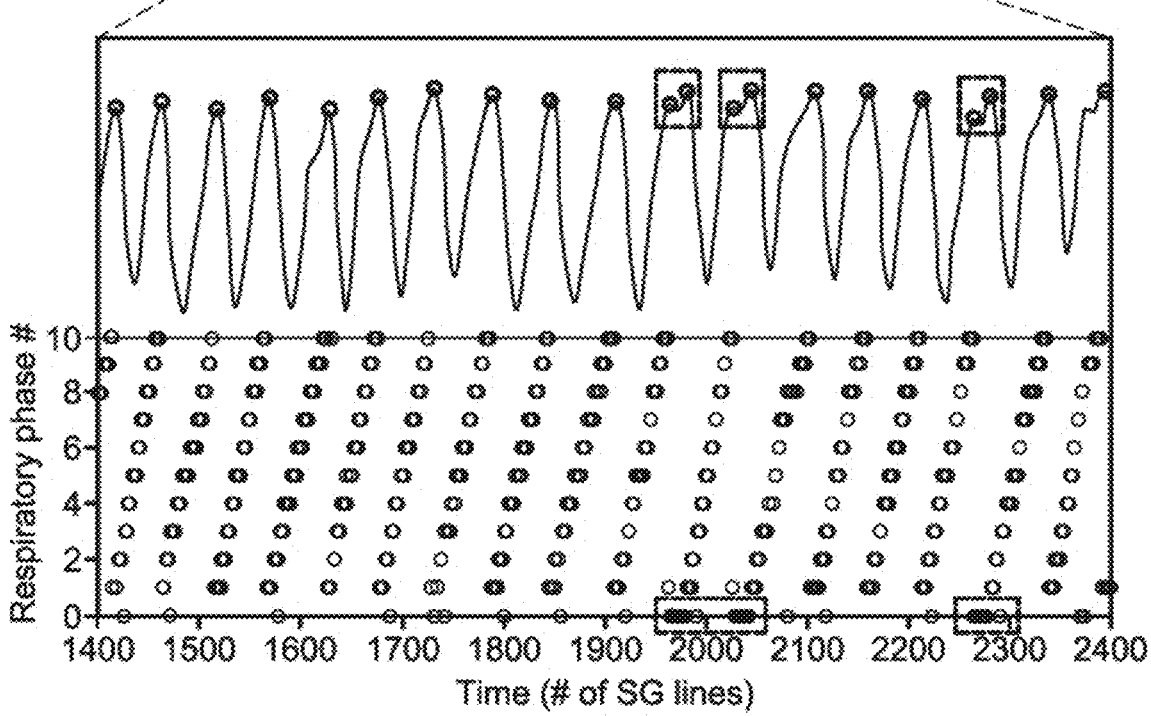

FIG. 3B
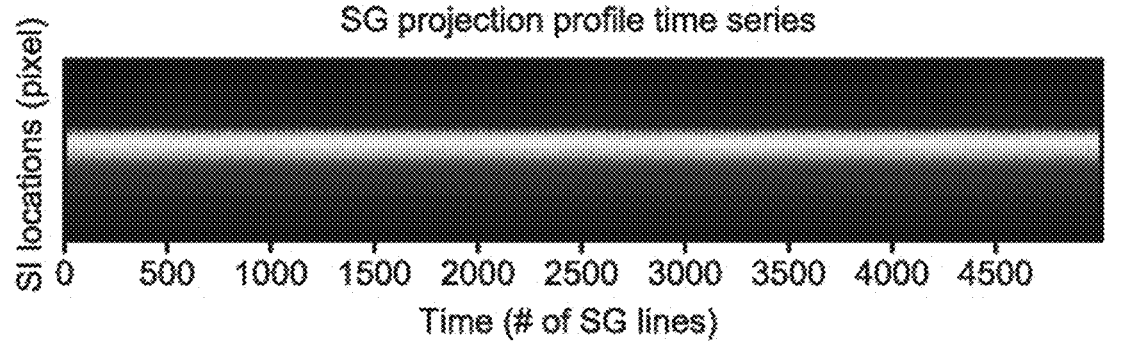
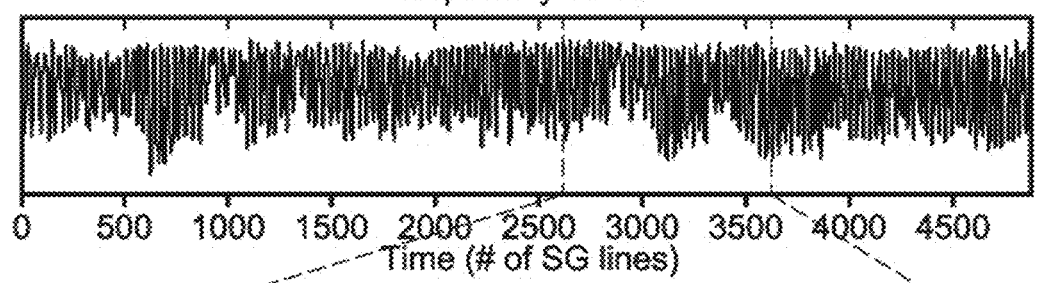
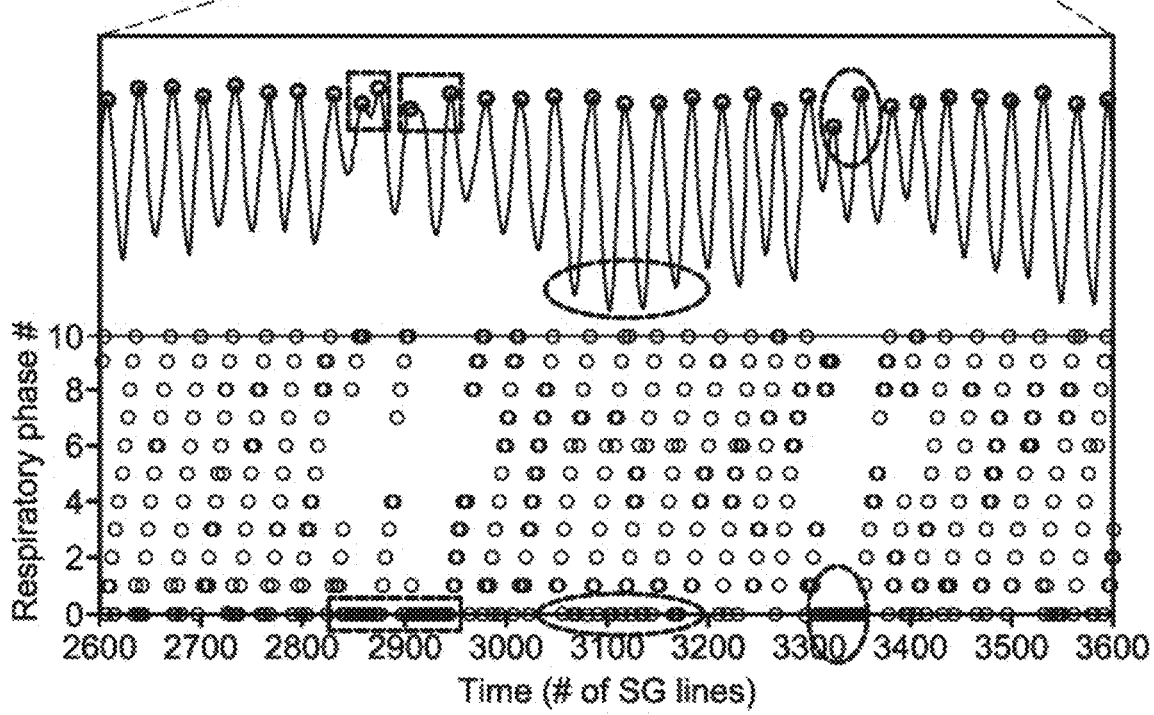

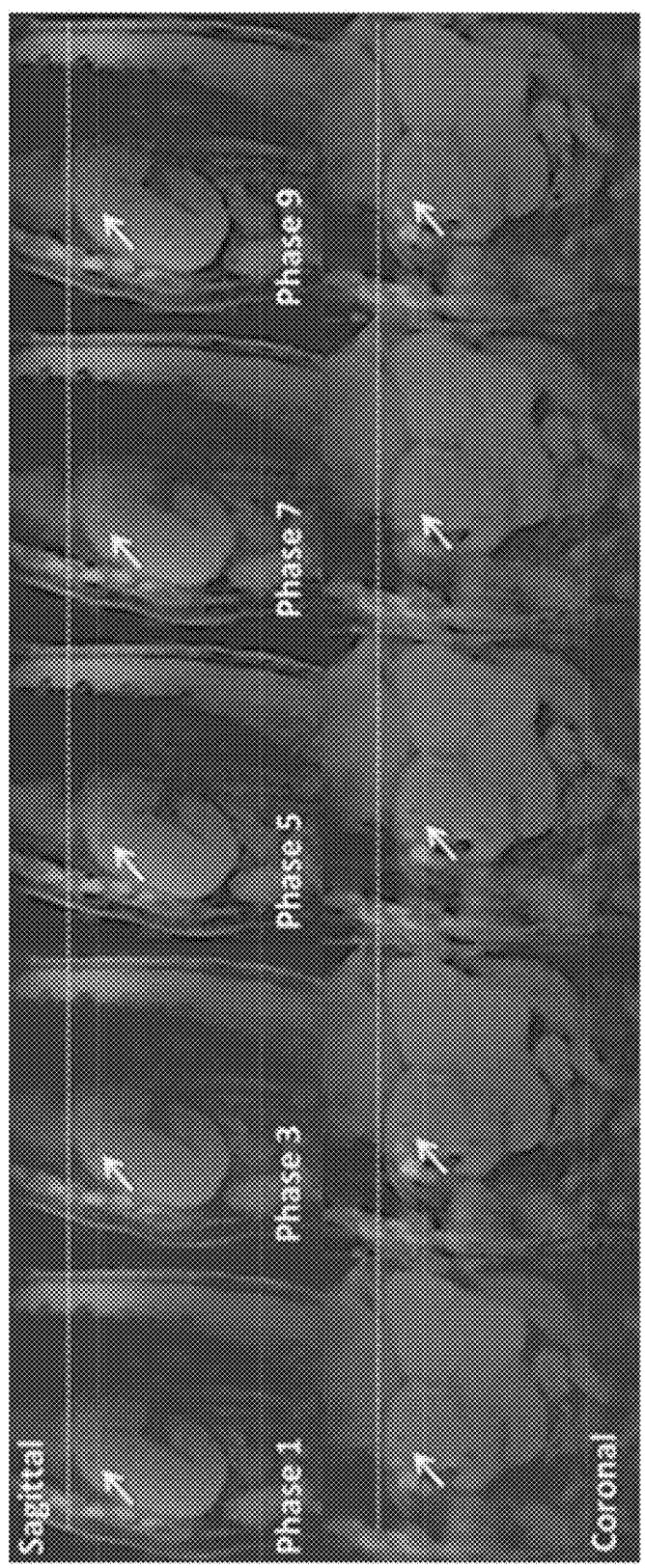
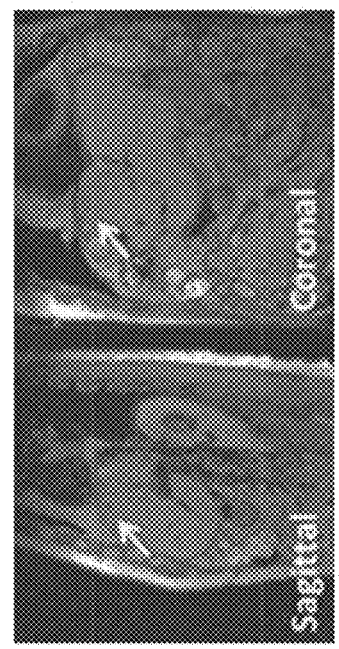
FIG. 6

FIG. 8
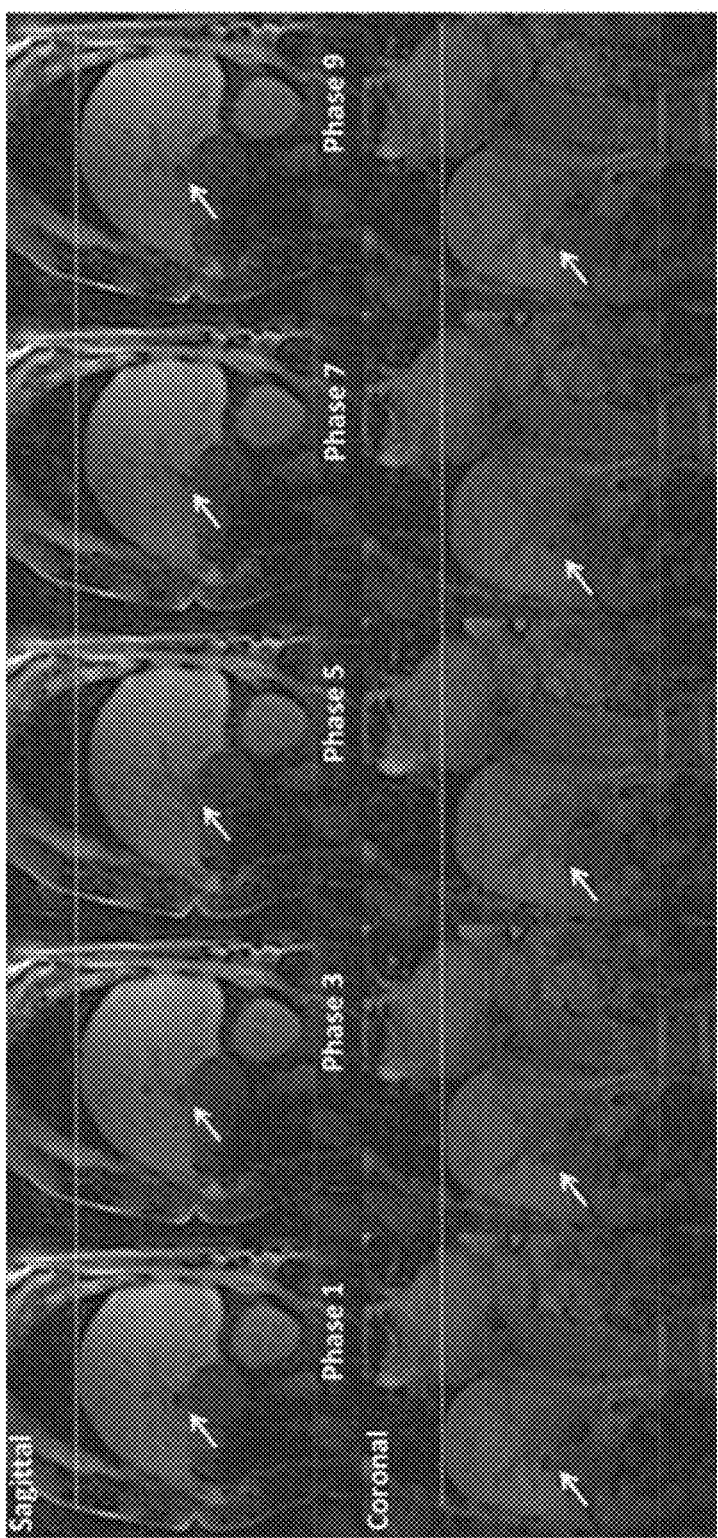
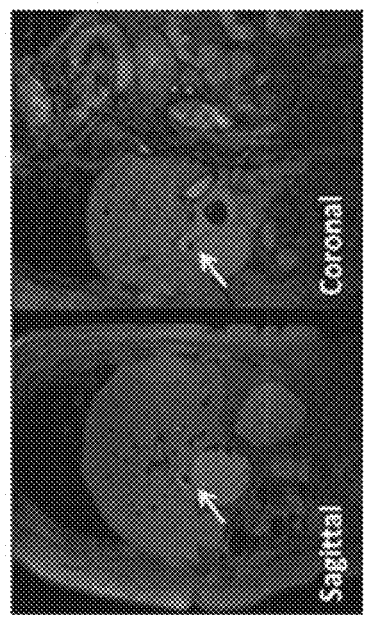

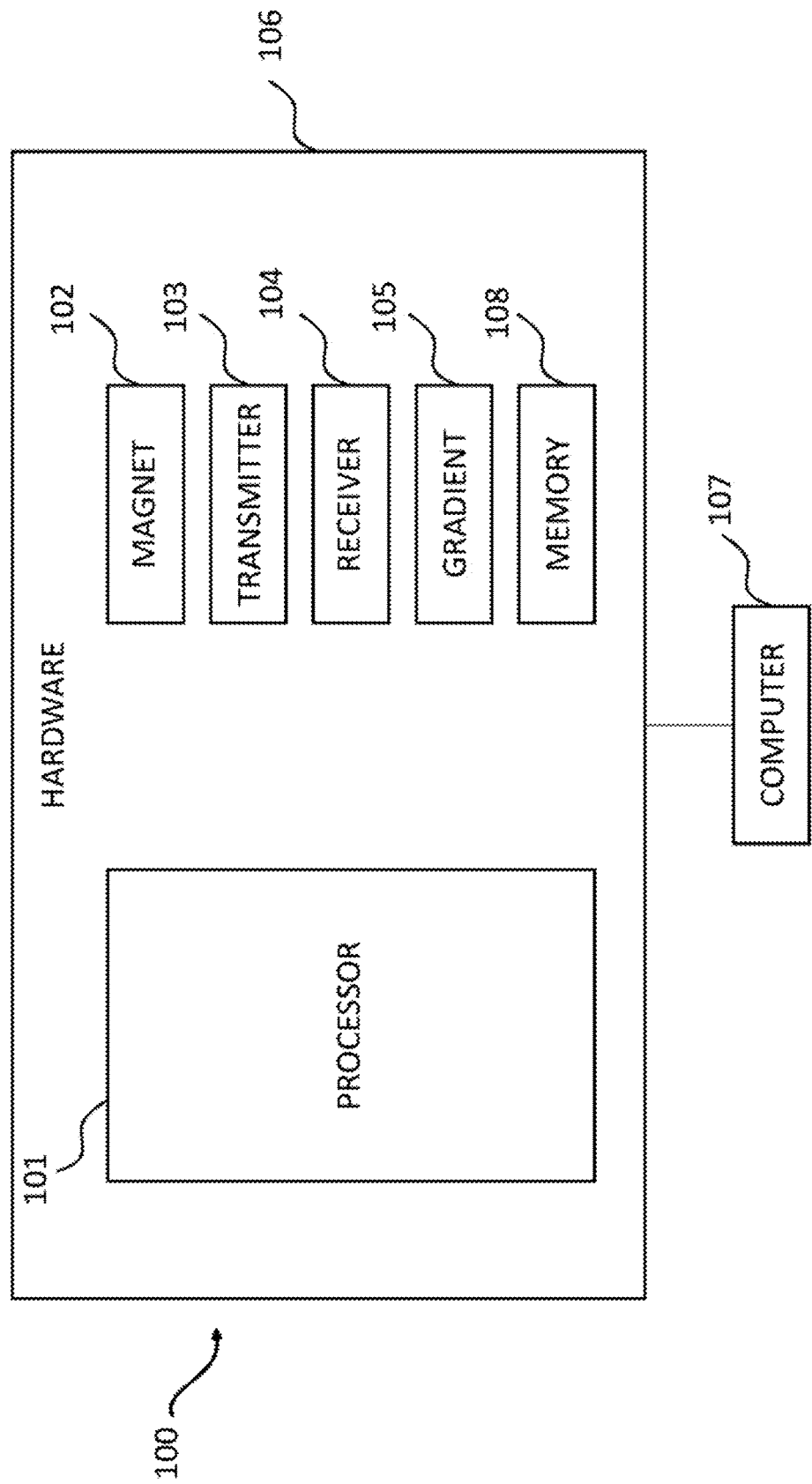

CHARACTERIZATION OF RESPIRATORY MOTION IN THE ABDOMEN USING A 4D MRI TECHNIQUE WITH 3D RADIAL SAMPLING AND RESPIRATORY SELF-GATING

FIELD OF THE INVENTION

The present invention generally relates to imaging methods and systems.

BACKGROUND

The following description includes information that may be useful in understanding the present invention. It is not an admission that any of the information provided herein is prior art or relevant to the presently claimed invention.

In free-breathing radiotherapy treatment planning, respiration-induced motion in abdominal organs poses significant challenges to accurate determination of treatment margins for target tumors. Inaccurate margin prescription may potentially result in under-dosage in tumors and/or over-dosage in healthy tissues, which may lead to poor treatment outcomes. As one of the important steps in the determination of treatment margins, the internal target volume (ITV), derived from the union of three-dimensional (3D) volumes of the tumor at all respiratory phases is needed to account for the variation of the tumor in position, shape, and size due to respiration (as described in Berthelsen A K. What's new in target volume definition for radiologists in ICRU Report 71? How can the ICRU volume definitions be integrated in clinical practice? Cancer Imaging 2007; 7:104-116, which is incorporated herein by reference in its entirety as though fully set forth). Moreover, the information on the spatial relationship in three dimensions between the tumor and surrounding healthy tissues is desirable to optimize radiation beam arrangement. The clinically standard approach to treatment planning is four-dimensional (4D) computed tomography (CT) that consecutively acquires a series of phase-resolved 2D slices and retrospectively sorts them into respiratory phase-resolved 3D image sets. However, 4D-CT has a number of limitations including: 1) high dose of ionizing radiation caused by repetitive irradiation at the same location necessary to image a complete respiratory cycle; 2) suboptimal tumor delineation due to poor soft tissue contrast; 3) and most importantly, susceptibility to manifest motion artifacts (i.e. resorting artifacts) caused by breathing pattern variation between individual 2D slice acquisitions.

As an alternative, magnetic resonance imaging (MRI) can also be used to generate respiratory phase or time-resolved images for treatment planning Real-time 2D-MRI has been utilized to collect cine-2D images from two orthogonal planes across the tumor center to help determine the 3D motion trajectories of the tumor. However, this approach may not fully characterize the 3D motion of the entire tumor, making it difficult to accurately calculate the ITV for irregularly-shaped or deformable tumors. In addition, healthy vulnerable tissues surrounding the tumor may not be fully defined. Therefore, 4D-MRI, or phase/time-resolved 3D-MRI, is more suitable. Various 4D-MRI techniques have been proposed in the past, which can be generally categorized into two classes: 1) real-time volumetric acquisitions using fast 3D sequences (as described in Blackall J M, Ahmad S, Miguel M E, McClelland J R, Landau D B, Hawkes D J. MRI-based measurements of respiratory motion variability and assessment of imaging strategies for radiotherapy planning Phys Med Biol 2006; 51:4147; Dinkel J, Hintze C, Tetzlaff R, Huber P E, Herfarth K, Debus J, Kauczor H U, Thieke C. 4D-MRI analysis of lung tumor motion in patients with hemidiaphragmatic paralysis. Radiotherapy and Oncology 2009; 91:449-454; and Plathow C, Klopp M, Schoebinger M, et al. Monitoring of Lung Motion in Patients With Malignant Pleural Mesothelioma Using Two-Dimensional and Three-Dimensional Dynamic Magnetic Resonance Imaging: Comparison With Spirometry. Investigative Radiology 2006; 41:443-448, all of which are incorporated herein by reference in their entirety as though fully set forth) and 2) retrospective data sorting using concurrently recorded internal or external respiratory motion surrogates (as described in Cai J, Chang Z, Wang Z, Segars W P, Yin F-F. Four-dimensional magnetic resonance imaging (4D-MRI) using image-based respiratory surrogate: A feasibility study. Medical Physics 2011; 38:6384-6394; Hu Y, Caruthers S D, Low D A, Parikh P J, Mutic S. Respiratory Amplitude Guided 4-Dimensional Magnetic Resonance Imaging. International Journal of Radiation Oncology*Biology*Physics 2013; 86:198-204; Tokuda J, Morikawa S, Hague H A, Tsukamoto T, Matsumiya K, Liao H, Masamune K, Dohi T. Adaptive 4D MR imaging using navigator-based respiratory signal for MRI-guided therapy. Magnetic Resonance in Medicine 2008; 59:1051-1061; Tryggestad E, Flammang A, Han-Oh S, Hales R, Herman J, McNutt T, Roland T, Shea SM, Wong J. Respiration-based sorting of dynamic MRI to derive representative 4D-MRI for radiotherapy planning Medical Physics 2013; 40:051909; Siebenthal von M, Székely G, Gamper U, Boesiger P, Lomax A, Cattin P. 4D MR imaging of respiratory organ motion and its variability. Phys Med Biol 2007; 52:1547; and Siebenthal von M, Cattin P, Gamper U, Lomax A, Székely G. 4D MR Imaging Using Internal Respiratory Gating. In: Duncan J S, Gerig G, editors. Medical Image Computing and Computer-Assisted Intervention-MICCAI 2005. Springer Berlin Heidelberg; 2005. pp. 336-343, all of which are incorporated herein by reference as though fully set forth). The real-time 3D techniques are limited by the achievable spatiotemporal resolution, which may cause blurring of the fine or fast-moving structures. In contrast, the sorting-based techniques alleviate this constraint by combining data that belong to the same respiratory phase yet acquired at different time points, hence resulting in a series of respiratory phase-resolved 3D images. Most of the techniques in the second class are based on multiple 2D acquisitions with prospective or retrospective respiratory gating followed by slice sorting. These 2D approaches have relatively low slice resolution of 5-10 mm, which may limit the accurate depiction of respiratory motion in the through-slice direction. More importantly, irregular breathing, commonly seen in patients, could potentially elicit unpredictable and prohibitively long scan times for the prospectively gated techniques and induce severe resorting artifacts, as in 4D-CT, for the retrospectively gated techniques. Recently, Buerger et al proposed to overcome these limitations by using a 3D acquisition with golden angle ordering in the phase-partition ($k_y$-$k_z$) plane followed by k-space sorting (see Buerger C, Clough R E, King A P, Schaeffter T, Prieto C. Nonrigid Motion Modeling of the Liver From 3-D Undersampled Self-Gated Golden-Radial Phase Encoded MRI. IEEE Trans. Med. Imaging 2012; 31:805-815; and Prieto C, Uribe S, Razavi R, Atkinson D, Schaeffter T. 3D undersampled golden-radial phase encoding for DCE-MRA using inherently regularized iterative SENSE. Magn Reson Med 2010; 64:514-526, both of which are incorporated herein by reference in their entirety as though fully set forth). The so called golden-radial phase encoding technique achieves high isotropic spatial resolution and offers improved robustness to irregular breathing by retrospective data sorting in k-space. This technique, however, is inherently limited in the respiratory motion-sampling rate (~250 ms), which could potentially result in errors in the respiratory curve during deep or fast breathing and hence large intra-phase motion variability. A higher motion-sampling rate would require either a smaller matrix size (sacrificing spatial resolution) or greater k-space undersampling in the $k_y$-$k_z$ plane.

There is a need in the art for improved imaging systems and methods that can accurately account for respiratory motion.

SUMMARY OF THE INVENTION

In various embodiments, the invention teaches a method for producing a set of images that depict motion of a tumor and/or non-tumor tissue by utilizing magnetic resonance imaging (MRI). In some embodiments, the method includes: (1) utilizing an MRI machine to apply a spoiled gradient echo sequence with a three-dimensional (3D) radial sampling k-space trajectory and one-dimensional (1D) projection-based self-gating (SG) to a volume of interest (VOI) including a tumor or portion thereof and/or an organ or portion thereof within a subject during a plurality of respiratory cycles; (2) acquiring magnetic resonance (MR) data from the subject, wherein the magnetic resonance data includes a plurality of sets of imaging lines, and wherein (a) each set of imaging lines is preceded by an SG line that serves as a motion stamp for the set of imaging lines it precedes, and (b) The Fourier Transform of the SG lines is sensitive to a respiratory organ motion in a specific direction; (3) utilizing the MR data to derive a respiratory curve that includes a plurality of time points, wherein each time point on the respiratory curve provides an index for the position of each imaging line along the specific direction; (4) sorting the k-space MR data into a plurality of respiratory phases, based on their relative temporal locations within a respiratory cycle; and (5) reconstructing an image for each of two or more of the plurality of respiratory phases by applying a conjugate gradient (CG) sensitivity encoding (SENSE) scheme with self-sensitivity calibration, thereby producing a set of images that collectively depict motion of the tumor and/or non-tumor tissue. In some embodiments, the 3D radial k-space is filled by utilizing 2D golden means ordering. In certain embodiments, one or more superior-inferior (SI) readout lines are inserted before every set of imaging lines. In some embodiments, every set of imaging lines includes an arbitrary number of imaging lines depending on the desired temporal resolution. In certain embodiments, a Fourier Transform of the SG lines is sensitive to respiratory organ motion in the SI direction. In some embodiments, the respiratory curve is derived by performing a principal component analysis (PCA) on a multi-channel projection profile time series, and the appropriate component is identified based on its major Fourier mode that matches a typical respiratory range. In certain embodiments, each time point on the derived respiratory curve provides an index for the SI position of each imaging line. In certain embodiments, band-pass filtering in the range of 0.125-0.5 Hz and peak detection is applied to the respiratory curve, wherein the peak corresponds to end-expiration, and (a) a respiratory cycle with abnormal duration or outlier end-expiratory location is discarded, and (b) each remaining cycle that does not meet those criteria is divided into a predetermined number of respiratory phases. In certain embodiments, each remaining cycle is evenly divided into an arbitrary number of respiratory phases depending on the clinical needs. In some embodiments, the MRI machine is a 3.0 T scanner. In certain embodiments, the subject is breathing irregularly and/or deeply compared to a normal subject during imaging. In some embodiments, the tumor is a cancerous tumor. In certain embodiments, the subject is a human.

In various embodiments, the invention teaches a magnetic resonance imaging (MRI) system. In some embodiments, the MRI system includes: (1) a magnet operable to provide a magnetic field; (2) a transmitter operable to transmit to a region within the magnetic field; (3) a receiver operable to receive a magnetic resonance signal from the region; (4) a processor operable to control the transmitter and the receiver; and (5) a non-transitory machine readable medium with instructions embedded thereon that when executed by a processor of an MRI machine and/or a computing machine capable of communicating electronically therewith cause the one or more processors to direct the transmitter and receiver to execute a sequence, that includes (a) applying a spoiled gradient echo sequence with a three-dimensional (3D) radial sampling k-space trajectory and one-dimensional (1D) projection-based self-gating (SG) to a volume of interest (VOI) that includes a tumor or portion thereof and/or an organ or portion thereof within a subject during a plurality of respiratory cycles; (b) acquiring magnetic resonance (MR) data from the subject, wherein the magnetic resonance data includes a plurality of sets of imaging lines, and wherein (i) each set of imaging lines is preceded by an SG line that serves as a motion stamp for the set of imaging lines it precedes, and (ii) The Fourier Transform of the SG lines is sensitive to a respiratory organ motion in a specific direction; and optionally (c) utilizing the MR data to derive a respiratory curve that includes a plurality of time points, wherein each time point on the respiratory curve provides an index for the position of each imaging line along the specific direction; (d) sorting the k-space MR data into a plurality of respiratory phases, based on their relative temporal locations within a respiratory cycle; and (e) reconstructing an image of each of the plurality of respiratory phases by applying a conjugate gradient (CG) sensitivity encoding scheme with self-sensitivity calibration, thereby producing a set of images that collectively depict motion of the tumor and/or non-tumor tissue.

In various embodiments, the invention teaches a non-transitory machine-readable medium having machine executable instructions for causing one or more processors of a magnetic resonance imaging (MRI) machine and/or a computing machine capable of electronic communication therewith to execute a method that includes: (1) utilizing an MRI machine to apply a spoiled gradient echo sequence with a three-dimensional (3D) radial sampling k-space trajectory and one-dimensional (1D) projection-based self-gating (SG) to a volume of interest (VOI) that includes a tumor or portion thereof and/or an organ or portion thereof within a subject during a plurality of respiratory cycles; (2) acquiring magnetic resonance (MR) data from the subject, wherein the magnetic resonance data includes a plurality of sets of imaging lines, and wherein (a) each set of imaging lines is preceded by an SG line that serves as a motion stamp for the set of imaging lines it precedes, and (b) The Fourier Transform of the SG lines is sensitive to a respiratory organ motion in a specific direction; (3) utilizing the MR data to derive a respiratory curve that includes a plurality of time points, wherein each time point on the respiratory curve provides an index for the position of each imaging line along the specific direction; (4) sorting the k-space MR data into a plurality of respiratory phases, based on their temporal locations within a respiratory cycle; and (5) reconstructing an image of each of the plurality of respiratory phases by applying a conjugate gradient (CG) sensitivity encoding scheme with self-sensitivity calibration, thereby producing a set of images that collectively depict motion of the tumor and/or non-tumor tissue. In some embodiments, the MRI machine is a 3.0 T machine. In some embodiments, the subject is a human. In certain embodiments, the tumor is a cancerous tumor.

BRIEF DESCRIPTION OF THE DRAWINGS

Exemplary embodiments are illustrated in the referenced figures. It is intended that the embodiments and figures disclosed herein are to be considered illustrative rather than restrictive.

FIG. 2 demonstrates, in accordance with an embodiment of the invention, a spoiled gradient recalled echo (GRE) sequence with 3DPR trajectory, 2D golden means ordering and one-dimensional (1D) self-gating (SG). (a) 4D-MRI imaging sequence showing each SG k-space group (dashed arrow) inserted in the superior-inferior (SI) direction at every segment of 15 radial projections, giving a temporal interval of ~98 ms between each SG group. A total of 73,005 projections were collected with 4867 SG lines after an approximately 8 minute scan. (b) 3D k-space trajectory showing data collection via radial 2D golden means ordering corresponding to (a). The radial lines collected in previous segments are grayed and the SG lines are represented via dashed arrows.

FIG. 3A and 3B demonstrate, in accordance with an embodiment of the invention, retrospective respiratory phase sorting in k-space demonstrated in a healthy volunteer (A) and a patient (B). The superior-inferior (SI) respiratory motion displacements represented in the respiratory curve were extracted via a principle component analysis (PCA) based method and served as a surrogate for respiratory phase throughout the acquisition (position index vs. time). Each peak (circle), representing end-expiration, was identified. Projection group outliers such as those involved in the respiratory cycles with abnormal time period (rectangle) and inconsistent expiratory amplitude (vertical oval) or those with large respiratory phase drift (horizontal oval) were discarded while only valid projection groups were assigned to respiratory phases between 1 and 10, shown as the black circles on the bottom graph. The healthy volunteer showed a relatively stable breathing pattern, while the patient showed occasional irregularities.

FIG. 6 depicts, in accordance with an embodiment of the invention, imaging of patient A. a) Phase-resolved sagittal and coronal images (phase 1, 3, ..., 9) reformatted from the 4D MRI image series showing well delineated gold fiducial (arrows) throughout the entire respiratory cycle. Dashed lines are drawn for better visualization of organ motion at each respiratory phase. b) A single frame of the corresponding real-time 2D-MRI image series.

FIG. 8 demonstrates, in accordance with an embodiment of the invention, imaging of patient B. a) Phase-resolved sagittal and coronal images (phase 1, 3, ..., 9) reformatted from the 4D MRI image series, showing well delineated tumor (arrows) throughout the entire respiratory cycle. Dashed lines are drawn for better visualization of organ motion at each respiratory phase. b) A single frame of the corresponding real-time 2D-MRI image series.

Figure 1:
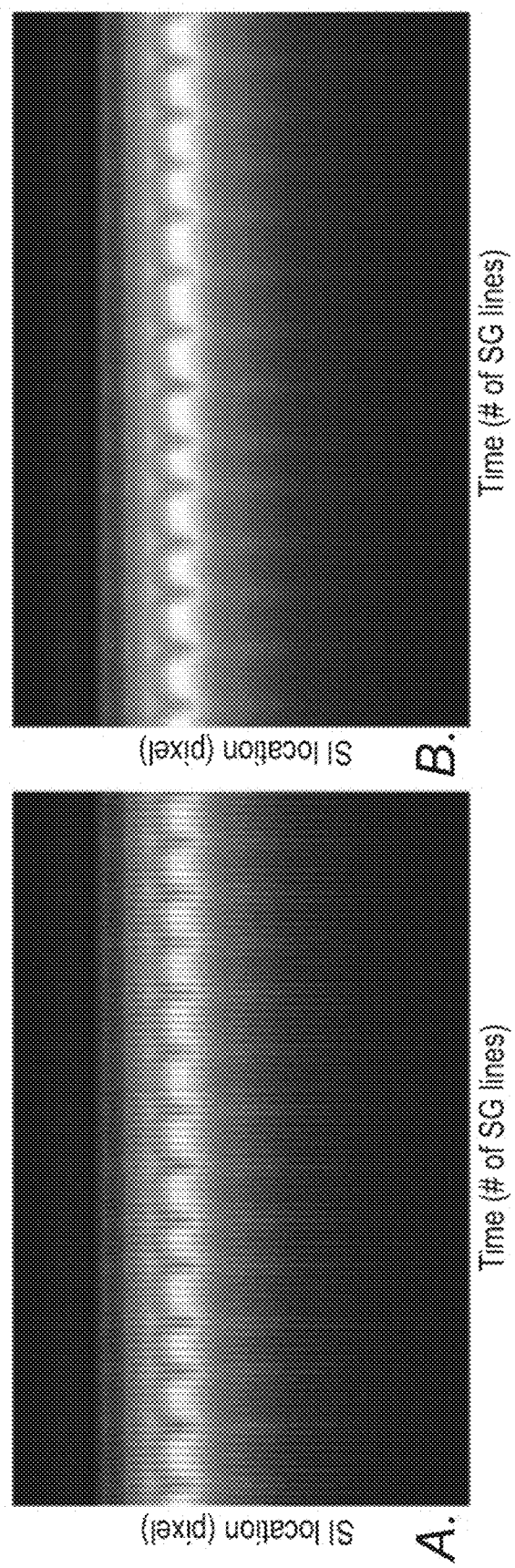
FIG. 1 demonstrates, in accordance with an embodiment of the invention, the sample Self-Gating (SG) projection profile time series for the first (a) and second (b) SG line. The effect of eddy current is apparent in the first SG series (a) (shown as the superimposed high frequency signal variation), which may reduce the robustness of motion estimation. This artifact is greatly suppressed in the second SG series (b).

FIG. 12 depicts a system in accordance with an embodiment of the invention.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Westbrook et al., *MRI in Practice* $4^{th}$ ed., and Guyton and Hall, *Textbook of Medical Physiology* $12^{th}$ ed., provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

Tumors that can be visualized and/or treated with radiation according to the embodiments described herein include those that are regularly shaped or irregularly shaped, those that are large, medium or small in size, and those that are located anywhere in the torso of a subject, including but not limited to a subject's chest or abdomen. The various embodiments described herein are especially effective when used to visualize organs and other tissues susceptible to motion, and especially respiratory motion. Non-limiting examples of targets in the abdomen affected by respiratory motion that have a clinically relevant diagnostic value include liver fibrosis, abdominal aortic aneurysm, pancreatic mass, and the like, each of which could also be advantageously visualized by the inventive systems and methods described herein.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term.

With the foregoing background in mind, in some embodiments the invention teaches a k-space sorting 4D-MRI technique based on a continuous 3D radial-sampling acquisition with 2D golden means ordering and a self-gating (SG) motion surrogate. In certain embodiments, the acquisition scheme enables arbitrary retrospective data sorting, frequent respiratory motion sampling, and is robust to k-space undersampling. Advantageously, this allows retrospective exclusion of the undesired respiratory outlier data and reconstruction of a respiratory phase-resolved 3D image series with isotropic high spatial resolution and an arbitrary number of temporal phases (ten in the reported examples described herein). The resultant image series permits the characterization of an average breathing motion pattern, which allows for accurate determination of the ITV, which can advantageously be used for radiation treatment planning, as described herein. Importantly, as described herein, the feasibility of using the technique to derive phase-resolved respiratory motion was demonstrated on a motion phantom and the livers of eight healthy volunteers and two patients. Greater detail regarding specific embodiments of the invention is provided herein below.

In various embodiments, the invention teaches a method for producing a series/set of images that depict motion of a tumor and/or non-tumor (e.g. organ) tissue utilizing magnetic resonance imaging (MRI). In some embodiments, the method includes utilizing an MRI machine to apply a spoiled gradient echo sequence with a three-dimensional (3D) radial sampling k-space trajectory and one-dimensional (1D) projection-based self-gating (SG) to a volume of interest (VOI) that includes a tumor or portion thereof and/or an organ or portion thereof within a subject during a plurality of respiratory cycles. In some embodiments, the method further includes acquiring magnetic resonance (MR) data from the subject, wherein the MR data includes a plurality of sets of imaging lines, and wherein (a) each set of imaging lines is preceded by an SG line that serves as a motion stamp for the set of imaging lines it precedes, and (b) The Fourier Transform of the SG lines is sensitive to a respiratory organ motion in a specific direction. In some embodiments, the method further includes utilizing the MR data to derive a respiratory curve that includes a plurality of time points, wherein each time point on the respiratory curve provides an index for the position of each imaging line along the specific direction. In some embodiments, the method further includes sorting the k-space MR data into a plurality of respiratory phases, based on their relative temporal locations within a respiratory cycle; and reconstructing an image for each of two or more of the plurality of respiratory phases by applying a conjugate gradient (CG) sensitivity encoding (SENSE) scheme with self-sensitivity calibration (as described and referenced herein in the "Examples" section), thereby producing a series/set of images that collectively depict motion of the tumor and/or non-tumor tissue.

In certain embodiments, the 3D radial k-space is filled by utilizing 2D golden means ordering, as described in greater detail in the examples set forth herein below. In some embodiments, the method includes inserting one or more superior-inferior (SI) readout lines before every set of imaging lines. In certain embodiments, each set of imaging lines includes an arbitrary number of imaging lines, depending on the desired temporal resolution. In some embodiments, a Fourier Transform of the SG lines is sensitive to respiratory organ motion in the SI direction. In certain embodiments, the respiratory curve is derived by performing a principal component analysis (PCA) on a multi-channel projection profile time series, and the appropriate component is identified based on its major Fourier mode that matches a typical respiratory range, as described in greater detail in the examples set forth herein. In some embodiments, each time point on the derived respiratory curve provides an index for the SI position of each imaging line. In some embodiments, band-pass filtering in the range of 0.125-0.5 Hz and peak detection is applied to the respiratory curve, and the peak corresponds to end-expiration. In some embodiments, a respiratory cycle with abnormal duration or outlier end-expiratory location is discarded, and each remaining cycle that does not meet those criteria is divided into a predetermined number of respiratory phases. In certain embodiments, each remaining cycle is evenly divided into an arbitrary number of respiratory phases, depending on the clinical needs. In some embodiments, the MRI machine is a 3.0 T scanner. In certain embodiments, the MRI machine is a 1.5 T scanner. In some embodiments, the subject on whom imaging is performed is breathing irregularly and/or deeply compared to a normal subject during imaging. In some embodiments, the tumor is a cancerous tumor. In certain embodiments, the subject imaged is a mammal. In some embodiments, the subject imaged is a human.

In some embodiments, the imaging parameters for the 4D-MRI techniques described herein are as follows: FOV= $(300 \text{ mm})^3$; prescribed spatial resolution=$(1.56 \text{ mm})^3$; flip angle=10°; TR/TE=5.8/2.6 ms; readout bandwidth=399 Hz/pixel; nonselective 1-2-1 water excitation RF pulse with a duration of 400 µs to suppress the bright fat signal (as described in Levitt M H. Composite pulses. Progress in Nuclear Magnetic Resonance . . . 1986; 18:61-122, which is incorporated herein by reference in its entirety as though fully set forth). The temporal footprint for each respiratory phase varies according to the subject's average breathing cycle duration, ranging from 300 to 500 ms.

In some embodiments imaging parameters for 4D-MRI could be: FOV=$(100-400 \text{ mm})^3$; prescribed spatial resolution=$(0.6-5.0 \text{ mm})^3$; flip angle=5-30°; TR/TE=3-6/1.5-4 ms; readout bandwidth=130-1300 Hz/pixel; nonselective 1-2-1 water excitation RF pulse with a duration of 400-800 µs to suppress the bright fat signal. In some embodiments, the temporal footprint for each respiratory phase varies according to the subject's average breathing cycle duration depending on the number of respiratory phases.

In various embodiments, the invention teaches a magnetic resonance imaging system that includes (1) a magnet operable to provide a magnetic field; (2) a transmitter operable to transmit to a region within the magnetic field; (3) a receiver operable to receive a magnetic resonance signal from the region; (4) a processor operable to control the transmitter and the receiver; and (5) a non-transitory machine readable medium with instructions embedded thereon that when executed by one or more processor of an MRI machine and/or a computing machine capable of communicating electronically therewith causes the one or more processors to direct the transmitter and receiver to execute a sequence that includes (a) applying a spoiled gradient echo sequence with a three-dimensional (3D) radial sampling k-space trajectory and one-dimensional (1D) projection-based self-gating (SG) to a volume of interest (VOI) that includes a tumor or portion thereof and/or an organ or portion thereof within a subject during a plurality of respiratory cycles; (b) acquiring magnetic resonance (MR) data from the subject, wherein the magnetic resonance data includes a plurality of sets of imaging lines, and wherein (i) each set of imaging lines is preceded by an SG line that serves as a motion stamp for the set of imaging lines it precedes, and (ii) The Fourier Transform of the SG lines is sensitive to a respiratory organ motion in a specific direction; and optionally (c) utilizing the MR data to derive a respiratory curve that includes a plurality of time points, wherein each time point on the respiratory curve provides an index for the position of each imaging line along the specific direction; (d) sorting the k-space MR data into a plurality of respiratory phases, based on their relative temporal locations within a respiratory cycle; and (e) reconstructing an image of each of the plurality of respiratory phases by applying a conjugate gradient (CG) sensitivity encoding (SENSE) scheme with self-sensitivity calibration, thereby producing a set of images that collectively depict motion of the tumor and/or non-tumor tissue over time. In some embodiments, all of the steps above, including those normally associated with data acquisition and those normally associated with image reconstruction are performed by the MRI machine. In some embodiments, one or more of the steps described above are performed by a machine capable of electronic communication with an MRI machine, as described in greater detail in the examples set forth herein. Merely by way of example, image reconstruction and additional steps can be performed on a traditional computing workstation with sufficient computing capabilities. The imaging data used for image reconstruction may be provided to the computing workstation by any mechanism known in the art, including but in no way limited to by a standard wireless or wired communication.

In various embodiments, the invention teaches a non-transitory machine-readable medium having machine executable instructions for causing one or more processors of a magnetic resonance imaging (MRI) machine and/or a computing machine capable of electronic communication therewith to execute a method that includes (1) utilizing an MRI machine to apply a spoiled gradient echo sequence with a three-dimensional (3D) radial sampling k-space trajectory and one-dimensional (1D) projection-based self-gating (SG) to a volume of interest (VOI) that includes a tumor or portion thereof and/or an organ or portion thereof within a subject during a plurality of respiratory cycles; (2) acquiring magnetic resonance (MR) data from the subject, wherein the magnetic resonance data includes a plurality of sets of imaging lines, and wherein (a) each set of imaging lines is preceded by an SG line that serves as a motion stamp for the set of imaging lines it precedes, and (b) The Fourier Transform of the SG lines is sensitive to a respiratory organ motion in a specific direction; (3) utilizing the MR data to derive a respiratory curve comprising a plurality of time points, wherein each time point on the respiratory curve provides an index for the position of each imaging line along the specific direction; (4) sorting the k-space MR data into a plurality of respiratory phases, based on their relative temporal locations within a respiratory cycle; and (5) reconstructing an image of each of the plurality of respiratory phases by applying a conjugate gradient (CG) sensitivity encoding (SENSE) scheme with self-sensitivity calibration, thereby producing a set of images that collectively depict motion of the tumor and/or non-tumor tissue. In some embodiments, the MRI machine is a 3.0 T machine. In some embodiments, the MRI machine is a 1.5 T machine.

One of skill in the art would readily appreciate that several different types of imaging systems could be used to perform the inventive methods described herein, including all of the types of imaging systems described in the examples and experiments set forth herein, as well as similar systems. Further, by way of non-limiting example, FIG. 12 depicts a view of a system 100 that can be used to accomplish the inventive methods. System 100 includes hardware 106 and computer 107. Hardware 106 includes magnet 102, transmitter 103, receiver 104, and gradient 105, all of which are in communication with processor 101. Magnet 102 can include a permanent magnet, a superconducting magnet, or other type of magnet. Transmitter 103 along with receiver 104, are part of the RF system. Transmitter 103 can represent a radio frequency transmitter, a power amplifier, and an antenna (or coil). Receiver 104, as denoted in the figure, can represent a receiver antenna (or coil) and an amplifier. In the example shown, transmitter 103 and receiver 104 are separately represented, however, in one example, transmitter 103 and receiver 104 can share a common coil. Hardware 106 includes gradient 105. Gradient 105 can represent one or more coils used to apply a gradient for localization.

Processor 101, in communication with various elements of hardware 106, includes one or more processors configured to implement a set of instructions corresponding to any of the methods disclosed herein above and below in the examples. Processor 101 can be configured to implement a set of instructions (stored in a memory 108 of hardware 106) to provide RF excitation and gradients and receive magnetic resonance data from a volume of interest (or target volume of interest).

Computer 107 is coupled to hardware 106. Computer 107 can include one or more of a desktop computer, a workstation, a server, or a laptop computer. In one example, computer 107 is user-operable and includes a display, a printer, a network interface or other hardware to enable an operator to control operation of the system 100. In alternative embodiments, a system can be configured in which a computer communicates wirelessly with the MRI machine to receive or send imaging data.

One skilled in the art will recognize many methods and materials similar or equivalent to those described herein, which could be used in the practice of the present invention. Indeed, the present invention is in no way limited to the methods and materials described.

Sequence Design

A spoiled gradient recalled echo (GRE) sequence with 3D radial-sampling k-space trajectory and one-dimensional (1D) projection-based SG was implemented at 3.0 T for image acquisition (see Pang J, Sharif B, Fan Z, Bi X, Arsanjani R, Berman D S, Li D. ECG and navigator-free four-dimensional whole-heart coronary MRA for simultaneous visualization of cardiac anatomy and function. Magn Reson Med 2014, which is incorporated herein by reference in its entirety as though fully set forth).

In an attempt to preserve the sampling pattern stability required for arbitrary retrospective data sorting, the 3D radial k-space was filled using the 2D golden means ordering (see Chan R W, Ramsay E A, Cunningham C H, Plewes D B. Temporal stability of adaptive 3D radial MRI using multidimensional golden means. Magnetic Resonance in Medicine 2009; 61:354-363, which is incorporated herein by reference in its entirety as though fully set forth), a generalization of the original golden-angle ordering for 2D radial imaging (see Winkelmann S, Schaeffter T, Koehler T, Eggers H, Doessel O. An Optimal Radial Profile Order Based on the Golden Ratio for Time-Resolved MRI. IEEE Trans. Med. Imaging 2007; 26:68-76, which is incorporated herein by reference in its entirety as though fully set forth). The polar and azimuthal angles were calculated using the following equations:

$$\theta_m = \cos^{-1}(\mathrm{mod}(m\varphi_1, 1)), \ m=1, 2, \ldots$$

$$\varphi_m = 2\pi \, \mathrm{mod}(m\varphi_2, 1), \ m=1, 2, \ldots$$

where $\varphi_1=0.4656$ and $\varphi_2=0.6823$ are the 2D golden means, $\theta$ is the polar angle, $\phi$ is the azimuthal angle, and m is the radial line index.

To detect respiratory motion, a group of two superior-inferior (SI) readout lines were inserted at every 15 imaging lines or an interval of approximately 98 ms (TR=5.8 ms). During acquisition, the large k-space jumps from imaging lines to SG lines caused apparent eddy-current artifacts (FIG. 1), which may reduce the robustness of motion estimation. To mitigate this effect, two consecutive SG lines were acquired and only the second SG line was used for respiratory motion monitoring (see Bieri O, Markl M, Scheffler K. Analysis and compensation of eddy currents in balanced SSFP. Magnetic Resonance in Medicine 2005; 54:129-137, which is incorporated herein by reference in its entirety as though fully set forth)

Similar to 4D-CT, in this particular embodiment the inventive technique aimed to construct ten respiratory phases. To achieve this within a reasonable scan time, a total of 73,005 imaging lines were acquired in 8 mins, as illustrated in FIG. 2. The choice of a fixed scan time, 8 min., is based on (a) preliminary testing on volunteers showing that usually approximately 5-15% data belong to irregular respiratory cycles and (b) previous experience on self-calibrating sensitivity encoding (SENSE) reconstruction of coronary arteries showing that an approximately 8-fold acceleration (based on the Nyquist rate $$N_{full} = \frac{\pi}{2} N^2,$$

with N being the number of readout points and $N_{full}$ being the total number of lines) is feasible for a ~1.0-mm spatial resolution (see Pang J, Sharif B, Arsanjani R, Bi X, Fan Z, Yang Q, Li K, Berman D S, Li D. Accelerated whole-heart coronary MRA using motion-corrected sensitivity encoding with three-dimensional projection reconstruction. Magnetic Resonance in Medicine 2014, which is incorporated herein by reference in its entirety as though fully set forth). Thus, it was anticipated that approximately 6000-7000 lines, after rejection of motion-corrupted data, would be available in each of the ten respiratory phases and reasonably adequate for reconstructing images with a lower spatial resolution (i.e. 1.56 mm).

Image Reconstruction

Extraction of the Respiratory Signal

Each SG line serves as a motion stamp for a segment of 15 imaging lines that follow. The Fourier Transform of the SG lines, essentially a projection of the imaging volume onto the SI axis, is sensitive to the respiratory organ motion in the SI direction (see Stehning C, Börnert P, Nehrke K, Eggers H, Stuber M. Free-breathing whole-heart coronary MRA with 3D radial SSFP and self-navigated image reconstruction. Magnetic Resonance in Medicine 2005; 54:476-480; and Larson A C, White R D, Laub G, McVeigh E R, Li D, Simonetti O P. Self-gated cardiac cine MRI. Magnetic Resonance in Medicine 2004; 51:93-102, both of which are incorporated herein by reference in their entirety as though fully set forth).

In order to automatically extract the respiratory curve, a principal component analysis (PCA) is performed on the multi-channel projection profile time series, and the appropriate component is identified based on its major Fourier mode that matched the typical respiratory (0.1-0.5 Hz) range (see Odille F, Uribe S, Batchelor P G, Prieto C, Schaeffter T, Atkinson D. Model-based reconstruction for cardiac cine MRI without ECG or breath holding. Magnetic Resonance in Medicine 2010; 63:1247-1257, which is incorporated herein by reference in its entirety as though fully set forth).

This process results in a motion signal (i.e. the respiratory curve) that is correlated to the SI translation from conventional template matching (see Pang J, Sharif B, Arsanjani R, Bi X, Fan Z, Yang Q, Li K, Berman D S, Li D. Accelerated whole-heart coronary MRA using motion-corrected sensitivity encoding with three-dimensional projection reconstruction. Magnetic Resonance in Medicine 2014; and Pang J, Bhat H, Sharif B, Fan Z, Thomson L E J, LaBounty T, Friedman J D, Min J, Berman D S, Li D. Whole-heart coronary MRA with 100% respiratory gating efficiency:

self-navigated three-dimensional retrospective image-based motion correction (TRIM). Magn Reson Med 2014; 71:67-74, both of which are incorporated herein by reference in their entirety as though fully set forth), as detailed in Pang et al (see Pang J, Sharif B, Fan Z, Bi X, Arsanjani R, Berman D S, Li D. ECG and navigator-free four-dimensional whole-heart coronary MRA for simultaneous visualization of cardiac anatomy and function. Magn Reson Med 2014, which is incorporated herein by reference in its entirety as though fully set forth). In this study, each time point on the derived respiratory curve provides an index for the SI position of each imaging line segment.

Data Sorting

The k-space segments are retrospectively sorted into its respective respiratory phases based on their relative temporal locations within a respiratory cycle, as illustrated in FIG. 3. To this end, the respiratory curve (i.e. SI-position-index vs. time) first undergoes band-pass filtering (0.125-0.5 Hz) and peak (corresponding to end-expiration) detection. The respiratory cycles with abnormal durations or outlier end-expiratory locations (i.e. outside±2 standard deviations from the mean duration or end-expiratory location) are discarded. Then, each remaining cycle is evenly divided into ten temporal respiratory phases, where each segment is assigned a nominal respiratory phase-index between 1 and 10. To reduce the intra-phase position variability, a more stringent position-index range, i.e. mean±standard deviation, was defined for each phase. All segments are then re-inspected for their position-index to determine its appropriate respiratory phase. The segment with its position-index falling out of the defined range will be re-assigned to a neighboring phase if the new range qualifies, or will otherwise be discarded. All thresholds for data sorting were kept constant for all subjects.

Image Reconstruction

After data sorting, each respiratory phase is reconstructed individually using a conjugate-gradient (CG) SENSE method with self-sensitivity calibration. The details of the CG SENSE reconstruction can be found in Pang et at (see Pang J, Sharif B, Arsanjani R, Bi X, Fan Z, Yang Q, Li K, Berman D S, Li D. Accelerated whole-heart coronary MRA using motion-corrected sensitivity encoding with three-dimensional projection reconstruction. Magnetic Resonance in Medicine 2014, which is incorporated herein by reference in its entirety as though fully set forth). Specifically, the reconstruction algorithm used 15 CG iterations along with Tinkonov (L2) regularization with a weight of 1e-10 to further reduce noise and residual streaking Image reconstruction was implemented offline using MATLAB (Mathworks, Natick, Mass.) with parallel computing toolbox on a workstation with a 12-core Intel Xeon CPU and 96 GB of memory. All parameters for image reconstruction were kept constant for all subjects.

The feasibility of the technique was demonstrated with motion phantom studies and in-vivo liver imaging studies. All scans were performed on a clinical 3.0 T MRI system (MAGNETOM Verio, Siemens Healthcare, Erlangen, Germany) equipped with a 32-channel receiver coil (Invivo, Gainesville, Fla., USA).

Study Design

Figure 4:
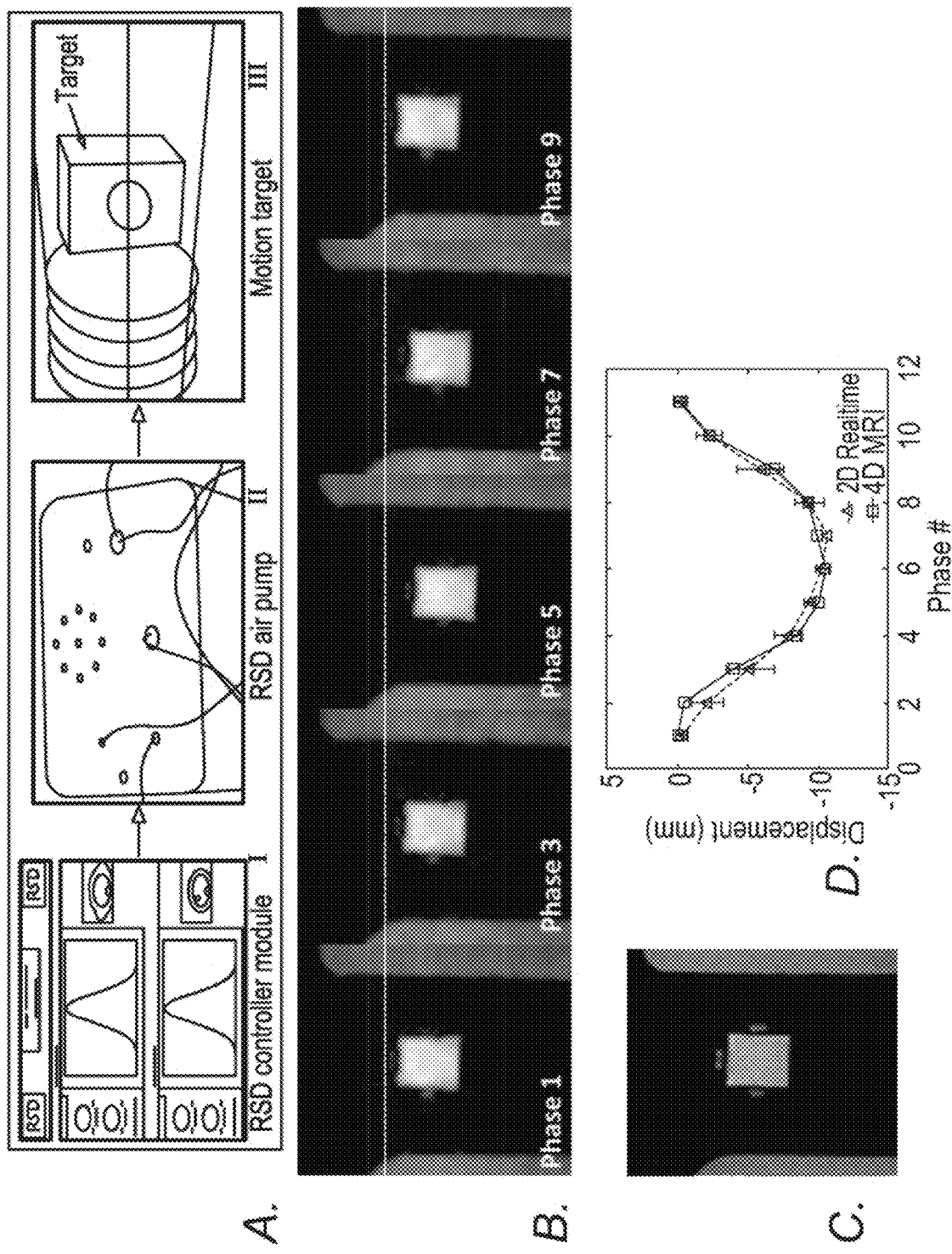
FIG. 4 depicts, in accordance with an embodiment of the invention, a phantom study. a) A commercial Dynamic Breathing Phantom system placed outside the MR scanner room (I) was used to produce simulation signals mimicking human respiratory motion. Through an air pump (II) and tube, the signals were used to drive a box filled by gadolinium-doped water, which served as an imaging target (III). During the scan, the box executed reciprocating motion along the z-axis of the magnet at a frequency of 18 cycles/min, giving a set of phase resolved images (phase 1, 3, ..., 9) reformatted from 4D-MRI, where the dashed line is drawn for a better visualization of the target motion at each respiratory phase (b). (c) A single frame of the real-time 2D-MRI image series. d) Measured SI displacement series, comparing between 4D-MRI and real-time 2D-MRI at each respiratory phase.
Figure 5:
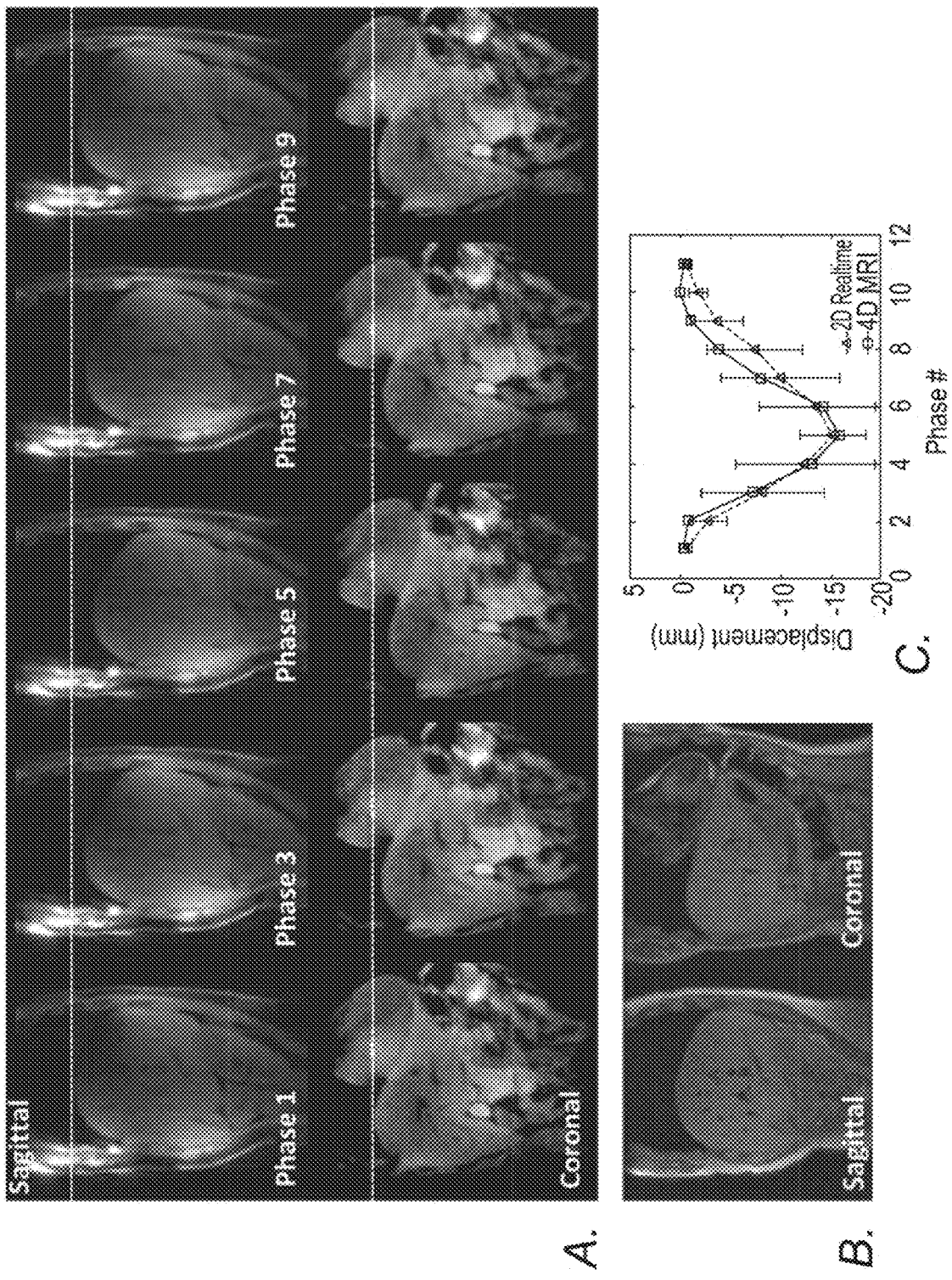
FIG. 5 depicts, in accordance with an embodiment of the invention, imaging of a healthy volunteer. a) Phase-resolved sagittal and coronal images (phase 1, 3, ..., 9) reformatted from the 4D MRI image series throughout the entire respiratory cycle. Dashed lines are drawn for better visualization of organ motion at each respiratory phase. b) A single frame of the corresponding real-time 2D-MRI image series. c) Measured SI displacement series, comparing between 4D-MRI and real-time 2D-MRI at each respiratory phase.

Schematics of the motion phantom are shown in FIG. 4a. A commercial Dynamic Breathing Phantom (RSD™, Long Beach, Calif., USA) system placed outside the scanner room was used to produce simulation signals that mimic the human respiratory motion. Through an air pump and tube, the signals were used to drive a plastic box (35×40×63 mm$^3$) fully filled with gadolinium-doped water and sealed with silicone sealant. Five PinPoint® fiducial markers (Beekley Medical™, Bristol, Conn., USA) were placed on each face of the box. The box was then used as an imaging target, where reciprocating motion was executed along the z-axis of the magnet at a frequency of 18 cycles/min.

Human studies were approved by the Cedars-Sinai Medical Center institutional review board and written consent was obtained prior to imaging. Eight healthy volunteers (four females, 23-48 years) and two clinical patients were recruited. Patient A (male, 77 years) diagnosed with hepatocellular carcinoma had a single lesion at the dome of the liver without evidence of additional metastatic lesions. A gold fiducial marker was placed next to the tumor for better visualization of respiratory motion in the 4D-CT images. The lesion had been treated with stereotactic body radiotherapy with a dose of 50 Gy in 5 fractions delivered every other day prior to the MRI study. Patient B (female, 85 years) had localized intrahepatic cholangiocarcinoma and was treated with concurrent gemcitabine-based chemoradiation therapy with a total radiation dose of 54 Gy in 30 fractions before the MRI study. All subjects were scanned under free breathing in a head-first supine position.

The imaging protocol consisted of a continuous 8-min 4D-MRI scan using the method described above and two 1-min single-slice real-time 2D-MRI scans (sagittal and coronal) using a conventional 2D Cartesian spoiled GRE sequence. Real-time 2D-MRI was used to derive the displacements of the imaging target in three orthogonal directions that served as a reference to evaluate the accuracy of the measurements from 4D-MRI. The isotropic imaging volume of 4D-MRI was centered on the moving phantom box or the liver. The imaging parameters for 4D-MRI were as follows: FOV=(300 mm)$^3$; prescribed spatial resolution= (1.56 mm)$^3$; flip angle=10°; TR/TE=5.8/2.6 ms; readout bandwidth=399 Hz/pixel; nonselective 1-2-1 water excitation RF pulse with a duration of 400 µs to suppress the bright fat signal (see Levitt M H. Composite pulses. Progress in Nuclear Magnetic Resonance . . . 1986; 18:61-122, which is incorporated herein by reference in its entirety as though fully set forth).

The temporal footprint for each respiratory phase varies according to the subject's average breathing cycle duration, ranging from 300 to 500 ms. Real-time 2D-MRI was performed with a slice that traversed the imaging target (i.e. phantom; healthy: liver; patient: A. fiducial or B. tumor) at a rate of 488 ms per frame for one minute. In-plane spatial resolution was matched to that of 4D-MRI, whereas slice thickness was 3 mm. All other parameters were also matched between 2D and 4D scans except that 2D scans used conventional fat saturation and dark blood (double-inversion) pre-pulses, and a TR/TE of 4.0/1.64 ms. The dark blood pre-pulse was used to avoid image artifacts arising from the inconsistent blood inflow in the 2D imaging plane. Fat suppression applied in both 2D-MRI and 4D-MRI was used to avoid obscuring of imaging targets by the high T1-weighted signals from fat.

Data Analysis

All images were loaded to a standard clinical workstation (Leonardo, Siemens Healthcare, Germany). From the two real-time 2D-MRI scans, the one that showed better delineation of the imaging target was chosen for analyses. From the 4D-MRI scan, a slice with location and thickness matched with 2D imaging was reconstructed from each of phase-resolved 3D image sets. The imaging target refers to the following locations: one of the fiducial markers attached to the moving phantom box, the dome of the right hemidiaphragm for the healthy volunteers, the gold fiducial in patient A, and the tumor in patient B.

Two-fold analyses were performed to evaluate the accuracy of the 4D-MRI derived motion displacements: 1) comparison of phase-resolved SI displacements between real-time 2D-MRI and 4D-MRI on the phantom, healthy volunteers, and patients; 2) comparison of phase-resolved displacement in SI, anterior-posterior (AP) and left-right (LR) directions between the two imaging scans on the two patients.

Phase-resolved motion displacements were directly measured for 4D-MRI. However, additional processing was required for real-time 2D-MRI that yielded time-resolved rather than phase-resolved displacements over multiple respiratory cycles. Specifically, the displacement time-series was first segmented into individual peak-to-peak respiratory cycles, each of which was then resampled to 11 time points, corresponding to 10 respiratory phases, as in 4D-MRI, and the first respiratory phase (starting peak) of the following respiratory cycle. By averaging the displacements from the same phase over all respiratory cycles, the 2D-MRI displacement at each respiratory phase was determined.

The 10 measured displacements obtained from the two imaging techniques were compared in regard to the motion amplitude, displacement difference (2D-MRI minus 4D-MRI) and absolute displacement difference averaged over 10 phases, as well as cross-correlation between phase-resolved displacements. The 3D motion trajectories for the two patients were also plotted to visualize respiratory hysteresis (see Seppenwoolde Y, Shirato H, Kitamura K, Shimizu S, van Herk M, Lebesque J V, Miyasaka K. Precise and real-time measurement of 3D tumor motion in lung due to breathing and heartbeat, measured during radiotherapy. International Journal of Radiation Oncology*Biology*Physics 2002; 53:822-834; and Kitamura K, Shirato H, Seppenwoolde Y, et al. Tumor location, cirrhosis, and surgical history contribute to tumor movement in the liver, as measured during stereotactic irradiation using a real-time tumor-tracking radiotherapy system. Int. J. Radiat. Oncol. Biol. Phys. 2003; 56:221-228, both of which are incorporated herein by reference in their entirety as though fully set forth).

Further, image sharpness was measured on all subjects for both 4D-MRI and real-time 2D-MRI to allow a quantitative evaluation of image quality. Specifically, on end-expiration images, the sharpness was measured and averaged over three locations across the lung-liver interface using the method proposed in Li et al (see Li D, Carr J C, Shea S M, Zheng J, Deshpande V S, Wielopolski P A, Finn J P. Coronary arteries: magnetization-prepared contrast-enhanced three-dimensional volume-targeted breath-hold MR angiography. Radiology 2001; 219:270-277, which is incorporated herein by reference in its entirety as though fully set forth) with an in-house MATLAB program.

In all tests, statistical significance was defined at the $p<0.05$ level. The paired Student's t-test was used to determine any difference and intraclass correlation coefficient (ICC) and cross-correlation were used to assess any agreement in measurements between the two techniques.

The SI motion of the imaging targets was well appreciated on the SG-derived respiratory curves. As expected, the motion phantom showed a strictly sinusoidal respiratory pattern and the human subjects, as illustrated in FIG. 3a (a healthy subject) and FIG. 3b (a patient), showed variations in breathing amplitude and frequency, with the patient showing more irregularity than the healthy volunteer. The retrospective data sorting strategy described in the examples above detected the breathing cycles with abnormal respiratory durations (rectangles on the zoom-in respiratory curve in FIG. 3) or expiratory peaks (vertical ovals) and also identified the outlier with large respiratory phase drift (horizontal oval). As a result, 5-16% of the total k-space data were discarded, with approximately 6000-7000 imaging lines available in each respiratory phase for image reconstruction.

The method in the non-limiting example set forth above offered respiratory phase-resolved volumetric coverage with a high isotropic spatial resolution, which allowed image reformatting for the visualization of respiratory organ motion at arbitrary location and orientation. Selected respiratory phases (1, 3, 5 . . . 9) of the motion phantom, a healthy volunteer and two patients in the coronal and sagittal orientations are shown in FIGS. 4b, 5a, 6a, and 8a, respectively. Compared with real-time 2D-MRI images (FIGS. 4c, 5b, 6b, and 8b), 4D-MRI images provided comparable visualization of the respiratory motion. No severe motion-induced image blurring was observed in each of the multiple phases, suggesting negligible intra-phase motion. The motion of the small fiducial or tumor in patients was clearly depicted in the 4D-MRI images as shown in FIGS. 6a and 8a, respectively. Compared with 2D real-time images, however, phase-resolved 3D images exhibited reduced overall image quality (e.g. signal inhomogeneity) and difference in tissue contrast. The reduction in image quality could be attributed to several factors related to the 3D acquisitions such as aggressive undersampling in some irregular-breathing subjects, large k-space jump-induced eddy-current effects, and suboptimal $B_0$ shimming-induced off-resonance effects. As a quantitative measure of image quality, sharpness were measured in both real-time 2D-MRI and 4D-MRI and showed comparable results among all subjects ($0.341\pm0.089$ mm$^{-1}$ vs. $0.359\pm0.064$ mm$^{-1}$, $p=0.492$). On one hand, the regularized non-Cartesian SENSE reconstruction from undersampled data inevitably results in a certain degree of image smoothing (see Pruessmann K P, Weiger M, Börnert P, Boesiger P. Advances in sensitivity encoding with arbitrary k-space trajectories. Magnetic Resonance in Medicine 2001; 46:638-651, which is incorporated herein by reference in its entirety as though fully set forth), therefore, the reconstructed spatial resolution was likely lower than the prescribed one. On the other hand, relatively low temporal resolution (488 ms) and low signal-to-noise ratio may affect the image sharpness in the real-time 2D-MRI images. While not wishing to be bound by one particular theory, in examples set forth herein, these factors appear to have been of comparable importance, leading to comparable sharpness values between the two techniques. While not wishing to be bound by one particular theory, the variation in tissue contrast could be due to the differences in the two data acquisition methods as mentioned in the above section. In 2D-MRI images, the blood in the arteries and veins were well suppressed by the dark blood pre-pulses, whereas in 4D-MRI images, the blood appeared gray since data were acquired during a steady state. In addition, water excitation pulses may resulted in different fat suppression performances in 4D-MRI images than the conventional fat saturation pulses used in 2D-MRI.

The phase-resolved SI displacements were compared between 4D-MRI and 2D-MRI. As summarized in Table 1, good agreement was observed. For SI motion amplitude, results in the phantom was 1.4% (0.15 mm) less in 2D-MRI, presumably due to a lower temporal resolution in the 2D-MRI scan that might not have fully captured the true respiratory amplitude. In human subjects, however, the difference in amplitude between the two scans ranged from −11% to +16% (−2.23 to +2.06 mm), potentially due to slight breathing pattern variations between 2D and 4D acquisitions. Overall, the SI motion amplitudes between 2D- and 4D-MRI were in a good agreement based on the intra-class correlation coefficient (ICC=0.935; P<0.001). When observing the displacement differences over all ten respiratory phases, the mean displacement difference was −0.12 mm in the phantom and ranged from −1.81-0.53 mm in humans. The mean absolute displacement difference was 0.64 mm and 0.58-1.81 mm for phantom and humans, respectively. Excellent cross-correlation between the displacements series from the 4D and 2D-MRI was observed in all studies, i.e. 0.985 for the phantom and an average of 0.964 for healthy volunteers and 0.938 for patients. The derived SI displacement series were visually comparable between the two scans, as shown in FIGS. 4d, 5c, 7a and 9a. The SI displacements measured from 4D-MRI images at each respiratory phase matched well with those from real-time 2D-MRI images, where the 4D-MRI displacements mostly fell within a range of ±1 standard deviation and all fell within a range of ±2 standard deviation of the phase-matched displacements across all cycles captured by the 1-min 2D-MRI scan.

TABLE 1

Summary of motion characterization in healthy volunteer and patient studies comparing 4D-MRI and real-time 2D-MRI.

|  |  | Mean Displacement Difference (mm) | Mean Absolute Displacement Difference (mm) | Correlation Coefficient (CC) |
|---|---|---|---|---|
| Volunteer | 1 | −0.566 | 1.038 | 0.968 |
|  | 2 | −0.973 | 1.409 | 0.974 |
|  | 3 | 0.004 | 1.381 | 0.971 |
|  | 4 | 0.530 | 0.748 | 0.962 |
|  | 5 | −1.814 | 1.814 | 0.944 |
|  | 6 | −0.298 | 0.676 | 0.985 |
|  | 7 | 0.156 | 0.581 | 0.937 |
|  | 8 | −0.680 | 1.035 | 0.968 |
| Patient | A | −0.760 | 1.156 | 0.938 |
|  | B | −0.226 | 0.829 | 0.938 |
| Mean ± SD |  | −0.463 ± 0.66 | 1.067 ± 0.39 | 0.959 ± 0.02 |

The phase-resolved AP and LR displacements in patient A and patient B were also compared between 4D-MRI and 2D-MRI. AP and LR displacements were relatively small compare to SI displacements as expected. The mean displacement difference between 4D and 2D-MRI over all ten respiratory phases were −1.59 (AP) and −0.74 mm (LR) for patient A and −1.20/−0.74 mm for patient B. Good cross-correlation between the displacements series from the 4D and 2D-MRI was observed, with 0.867 (AP) and 0.724 (LR) for patient A and 0.785 and 0.815 for patient B. The derived AP/LR displacement series were visually comparable between the two scans as represented in FIGS. 7b/c (Patient A) and 9b/c (Patient B).

Figure 7:
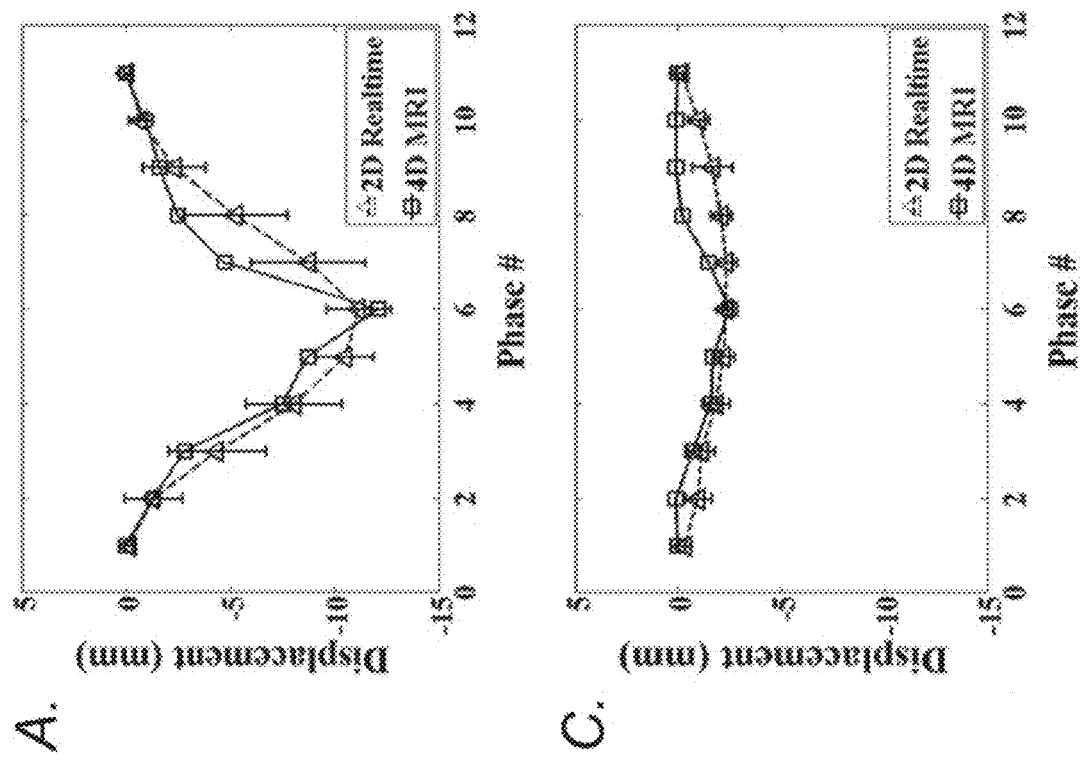
FIG. 7 demonstrates, in accordance with an embodiment of the invention, imaging of patient A. a-c) Measured displacement series, comparing between 4D-MRI and real-time 2D-MRI at each respiratory phase for SI (a), AP (b), and LR (c) directions. d) 3D visualization of the fiducial trajectories over ten respiratory phases, showing the hysteresis effect.
Figure 9:
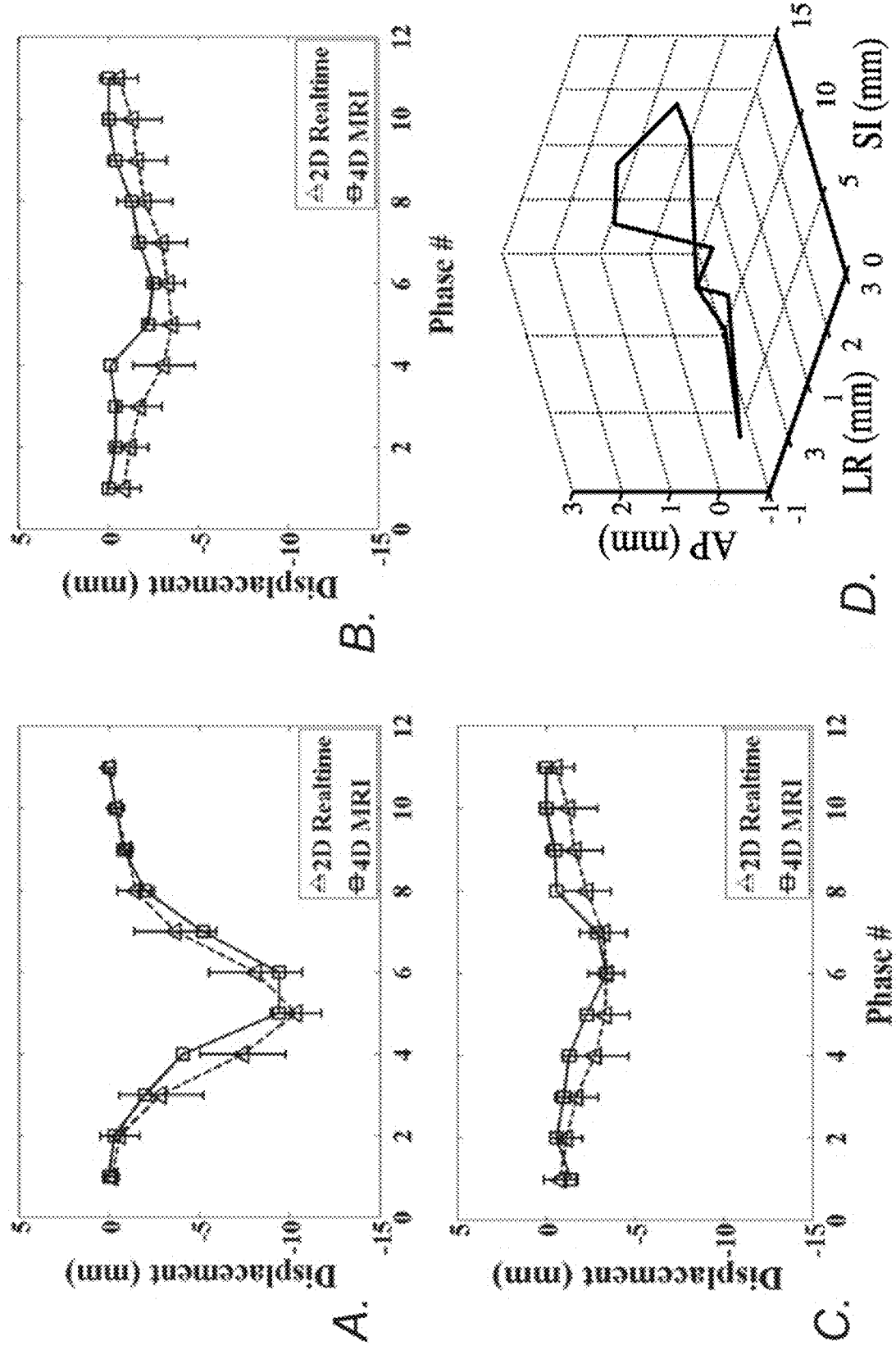
FIG. 9 demonstrates, in accordance with an embodiment of the invention, imaging of patient B. a-c) Measured displacement series, comparing between 4D-MRI and real-time 2D-MRI at each respiratory phase for SI (a), AP (b), and LR (c) directions. d) 3D visualization of the tumor trajectories over ten respiratory phases, showing the hysteresis effect.
Figure 10:
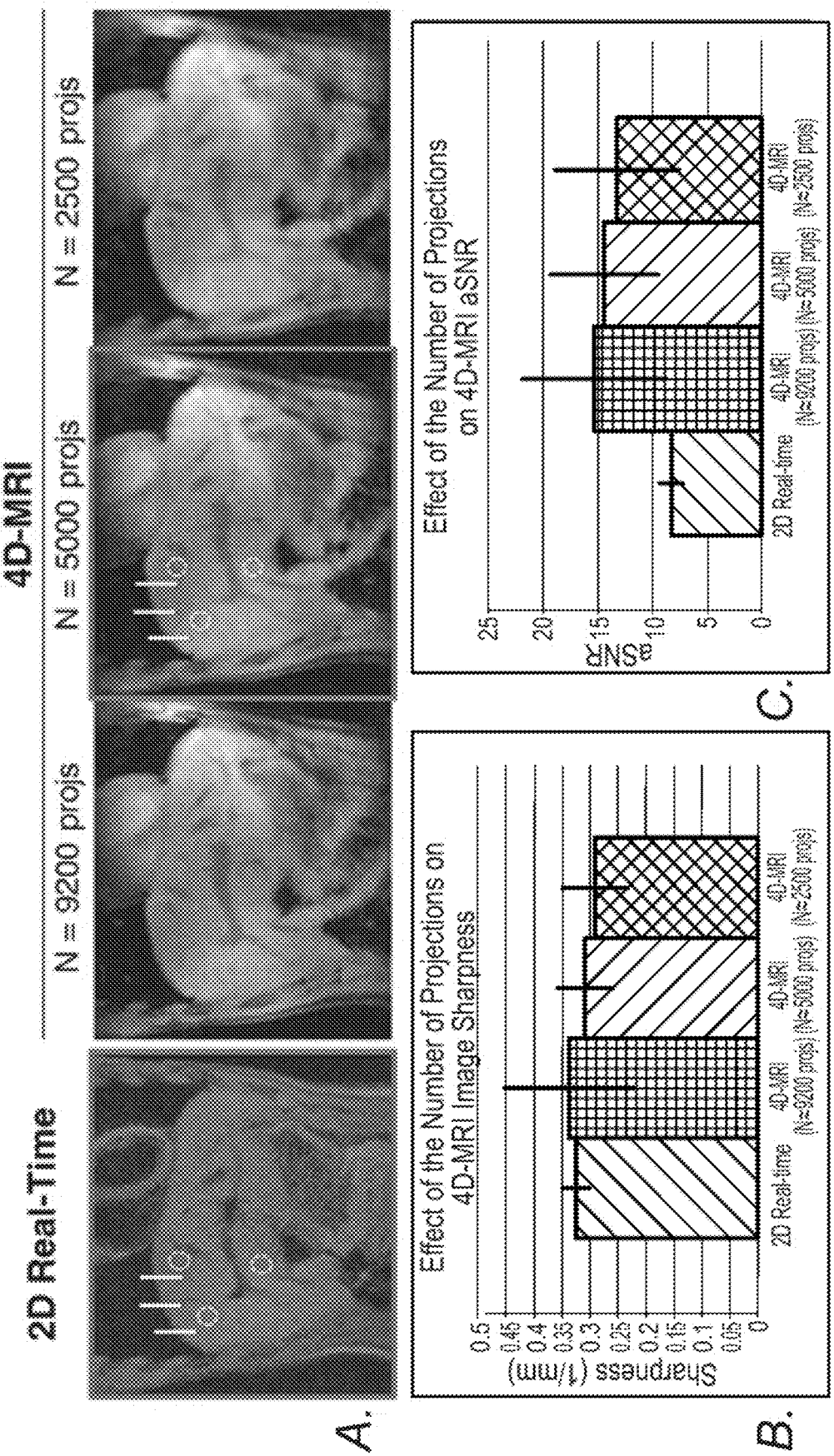
FIG. 10 demonstrates, in accordance with an embodiment of the invention, the effect of the number of projections on 4D-MRI image quality. a) 2D real-time image during end-expiration vs. the matched respiratory phase and slice location from the 4D image series, reconstructed using CG-SENSE from 9200, 5000, and 2500 projections, respectively. The data was retrospectively extracted from a single 12 min scan (a total of 120,000 projections). b) Image sharpness of different images, measured at various locations on the lung-liver interface, as indicated by the yellow vertical lines in (a). c) Apparent signal-to-noise ratio (aSNR) of different lambdas, measured at various locations on the liver as indicated by the circles in (a). With fewer projections, both sharpness and aSNR gradually reduced as can be appreciated both visually and from the measured values.
Figure 11:
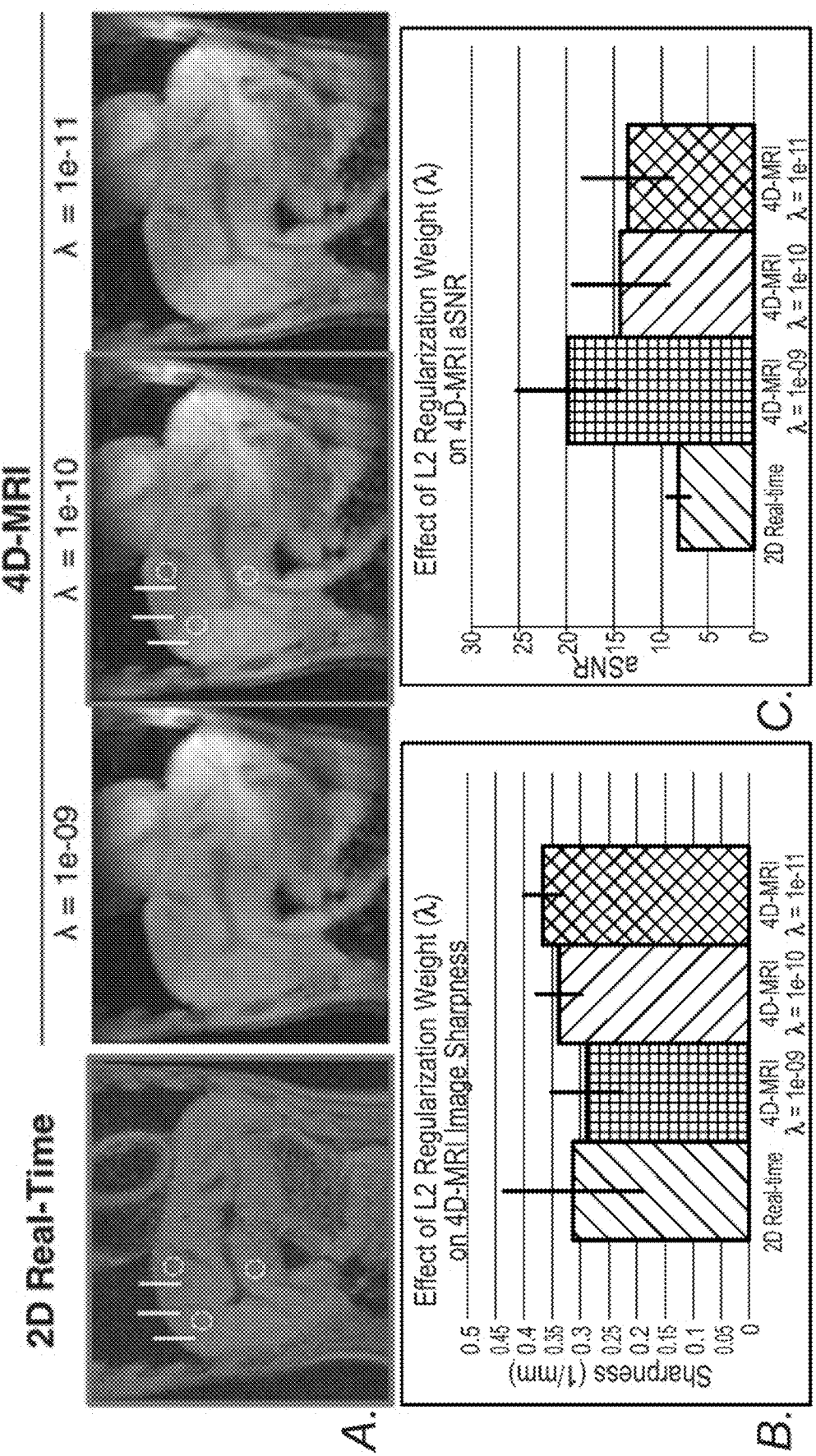
FIG. 11 demonstrates, in accordance with an embodiment of the invention, the effect of L2 regularization weight ($\lambda$) on 4D-MRI image sharpness. a) 2D real-time image during end-expiration vs. the matched respiratory phase and slice location from the 4D image series, reconstructed with 5000 projections using CG-SENSE and different values of λ. b) Mean image sharpness averaged from various locations on the lung-liver interface, as indicated by the yellow vertical lines in (a). c) Apparent signal-to-noise ratio (aSNR) values, measured at various locations on the liver as indicated by the circles in (a). As λ decreased, sharpness increased and the aSNR decreased, as can be seen both visually and from the numerical comparisons.

In addition, the hysteresis effects for both patients are illustrated in FIGS. 7d (patient A) and 9d (patient B). The 3D trajectories clearly revealed the different paths of inspiration and expiration for the structure of interest.

4D imaging is of interest to the radiation therapy community aiming at focusing a high radiation dose to moving tumors while sparing surrounding normal tissues. Phase-resolved target definition and motion management in three dimensions can be derived from 4D imaging, allowing determination of the ITV in clinical practice. 4D imaging also facilitates better appreciation of the spatial relation between tumors and surrounding tissues at each respiratory phase. This would impact future clinical practice by allowing more optimal treatment margins for individual respiratory phases and/or selection of the best phases for minimal radiation dose delivery to normal tissues, which are both intended to be embodiments of methods of the present invention (see Rietzel E, Chen G T Y, Choi N C, Willet C G. Four-dimensional image-based treatment planning: Target volume segmentation and dose calculation in the presence of respiratory motion. International Journal of Radiation Oncology*Biology*Physics 2005; 61:1535-1550; and Hof H, Rhein B, Haering P, Kopp-Schneider A, Debus J, Herfarth K. 4D-CT-based target volume definition in stereotactic radiotherapy of lung tumours: Comparison with a conventional technique using individual margins. Radiotherapy and Oncology 2009; 93:419-423, both of which are incorporated herein by reference in their entirety as though fully set forth).

4D-MRI is recently gaining more interests due to its excellent soft-tissue contrast and the lack of ionizing radiation as opposed to 4D-CT. However, due to various technical limitations of the existing techniques as mentioned previously, 4D-MRI has not been widely adopted in radiotherapy treatment planning The non-limiting examples set forth above describe a novel self-gated 4D-MRI technique to overcome those limitations and make 4D-MRI amenable to translate into a clinical setting. Experience from motion phantom and in-vivo liver imaging studies indicates that accurate respiratory motion characterization can be achieved through the respiratory phase-resolved 3D image series obtained from the technique.

The 3D radial acquisition offered a high isotropic spatial resolution for visualizing fine anatomic features, such as liver fiducials, from arbitrary perspectives (FIG. 6a). Furthermore, the 2D golden means k-space ordering offered quasi-uniform k-space sampling for each respiratory phase as well as flexible k-space data sorting and rejection, which is important for consistent image quality throughout all respiratory phases. A related strategy has recently been proposed for respiratory phase-resolved liver imaging using a radial-like phase and partition encoding ordering (see Buerger C, Clough R E, King A P, Schaeffter T, Prieto C. Nonrigid Motion Modeling of the Liver From 3-D Undersampled Self-Gated Golden-Radial Phase Encoded MRI. IEEE Trans. Med. Imaging 2012; 31:805-815, which is incorporated herein by reference in its entirety as though fully set forth). However, the approach described in the examples set forth above allows for a higher and more flexible SG motion-sampling rate throughout the acquisition that could translate to more precise motion estimation. Studies have demonstrated the feasibility of sampling respiratory motion at approximately every 98 ms, yet higher sampling rates are readily achievable with a slight penalty in scan time, and therefore are within the scope of embodiments of the present invention.

The detection of respiratory motion via SG, unlike the external (e.g. pneumatic devices) or internal (e.g. respiratory navigator) motion surrogates used in existing 4D-MRI methods, originates directly from the imaging volume and, in theory, may yield a more accurate motion estimate of the imaging target. By using the same excitation RF pulse and imaging parameters, the SG readouts are equivalent to the imaging readouts and, unlike respiratory navigators, do not disrupt the magnetization steady-state. Moreover, SG also eliminates the dark saturation bands usually seen on the liver from the respiratory navigator, which can be undesirable when the liver is the organ of interest. The regular and irregular breathing patterns in human subjects were clearly revealed by both the SG projection series and the SG-derived respiratory curves (FIG. 3). The effectiveness of SG was also corroborated by the excellent agreement between the respiratory displacements derived from 4D-MRI images and those derived from real-time 2D-MRI in all studies.

It is also noteworthy that the technique described in the examples set forth herein above utilized k-space sorting in a temporally binned fashion. For previous slice sorting-based techniques, irregular breathing episodes during scanning presented adverse effects on the scan duration and resulting image quality. The retrospective k-space sorting-based technique allows for the exclusion of irregular breathing cycles after scanning and facilitates the reconstruction of an averaged phase-resolved volumetric image series that is robust against irregular breathing patterns and maintains image quality. Meanwhile, the combination of 3D radial-sampling and CG-SENSE image reconstruction makes the k-space sorting approach more tolerable to high undersampling factors, which in turn helps maintain consistent image quality throughout all respiratory phases and subjects. Furthermore, the temporal binning strategy, achieved by using a high motion-sampling rate, allows for a uniformly distributed k-space throughout all respiratory phases. An additional advantage with temporal binning rather than SI position binning is the detection of hysteresis within the breathing cycle. Studies have demonstrated the 3D visualization of the hysteresis trajectories in patients.

The performance of the method described in the examples set forth above can be further modified to improve imaging under certain conditions. The imaging parameters described in the non-limiting examples set forth above may not be optimal for all subjects. For example, a fixed scan time of 8 min was prescribed in all studies, additional imaging lines would be better for subjects with highly irregular breathing patterns at the expense of longer scan times. The image reconstruction strategy described in the non-limiting examples set forth herein above utilized approximately 73,005 projections for adequate image quality, and each respiratory phase was reconstructed independently. Further acceleration could be achieved through exploiting the spatiotemporal correlation in the multi-channel dataset (see Sharif B, Bresler Y. AFFINE-CORRECTED PARADISE: FREE-BREATHING PATIENT-ADAPTIVE CARDIAC MRI WITH SENSITIVITY ENCODING. IEEE; 2007 pp. 1076-1079; Sharif B, Derbyshire J A, Faranesh A Z, Bresler Y. Patient-adaptive reconstruction and acquisition in dynamic imaging with sensitivity encoding (PARADISE). Magnetic Resonance in Medicine 2010; 64:501-513; Hansen M S, Baltes C, Tsao J, Kozerke S, Pruessmann K P, Eggers H. k-t BLAST reconstruction from non-Cartesian k-t space sampling. Magnetic Resonance in Medicine 2006; 55:85-91; Kim D, Dyvorne H A, Otazo R, Feng L, Sodickson D K, Lee V S. Accelerated phase-contrast cine MRI using k-t SPARSE-SENSE. Magnetic Resonance in Medicine 2012; 67:1054-1064; Jung H, Sung K, Nayak K S, Kim E Y, Ye J C. k-t FOCUSS: A general compressed sensing framework for high resolution dynamic MRI. Magnetic Resonance in Medicine 2009; 61:103-116; and Tsao J, Boesiger P, Pruessmann K P. k-t BLAST and k-t SENSE: Dynamic MRI with high frame rate exploiting spatiotemporal correlations. Magnetic Resonance in Medicine 2003; 50:1031-1042, all of which are incorporated herein by reference in their entirety as though fully set forth) which could help improve image quality (e.g. extreme respiratory irregularity cases where more data need to be discarded during data sorting), temporal resolution or reduce the total scan time. For image acquisition large gradient jumps in k-space could cause eddy-current effects that could potentially degrade image quality. Further developments in smoother k-space trajectories to minimize these effects are desirable. In addition, while not wishing to be bound by any one particular theory, the off-resonance due to $B_0$ inhomogeneity was perhaps one of factors accounting for image artifacts as the volumetric acquisition required a much larger shimming volume than the 2D protocol, which may degrade the shimming quality. Careful $B_0$ shimming is required and targeted excitation volume could help alleviate these artifacts by suppressing the signal from anatomic structures far away from the isocenter. Furthermore, the pulse sequence set forth in the non-limiting examples above used a spoiled GRE readout that offered primarily $T_1$-weighted image contrast. $T_2$-weighting, however, can also be used for tumor delineation, and could therefore be incorporated in embodiments of the inventive method (see Hu Y, Caruthers S D, Low D A, Parikh P J, Mutic S. Respiratory Amplitude Guided 4-Dimensional Magnetic Resonance Imaging. International Journal of Radiation Oncology*Biology*Physics 2013; 86:198-204, which is incorporated herein by reference in its entirety as though fully set forth). Means to include $T_2$-weighting to the image contrast, such as balanced steady-state free precession acquisition (see Benkert T, Bartsch A J, Blaimer M, Jakob P M, Breuer F A. Generating multiple contrasts using single-shot radial T 1sensitive and insensitive steady-state imaging. Magnetic Resonance in Medicine 2014; Derakhshan J J, Nour S G, Sunshine J L, Griswold M A, Duerk J L. Resolution enhanced T1-insensitive steady-state imaging. Magnetic Resonance in Medicine 2011; 68:421-429; and Schmitt P, Jakob P M, Kotas M, Flentje M, Haase A, Griswold MA. T-one insensitive steady state imaging: A framework for purely T2-weighted TrueFISP. Magnetic Resonance in Medicine 2011; 68:409-420, all of which are incorporated herein by reference in their entirety as though fully set forth) or $T_2$-preparation techniques, could also be utilized.

As demonstrated in the non-limiting examples set forth herein above, a self-gated 4D-MRI technique has been developed for the characterization of respiratory motion in abdominal organs. The studies reported in the non-limiting examples set forth herein above demonstrated its feasibility in providing respiratory phase-resolved 3D images with several advantages over existing 4D-MRI methods. This approach could be utilized as a viable alternative solution for the assessment of the impact of breathing on tumor and normal tissue motion, and thus help improve the precision of radiotherapy treatment planning Merely by way of non-limiting example, 4D-MRI could derive the motion trajectories of the individual voxels for both tumors and healthy surrounding tissues throughout a respiratory cycle. This would potentially help facilitate a better appreciation of the spatial relation between tumors and surrounding tissues at each respiratory phase, thus allowing more optimal treatment margins for individual respiratory phases or selection of the best phases for minimal radiation dose delivered to normal tissues.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for producing a set of images that depict motion of a tumor and/or non-tumor tissue utilizing magnetic resonance imaging (MRI), comprising:

utilizing an MRI machine to apply a spoiled gradient echo sequence with a three-dimensional (3D) radial sampling k-space trajectory and one-dimensional (1D) projection-based self-gating (SG) to a volume of interest (VOI) comprising (i) a tumor, (ii) a portion of the tumor, (iii) an organ, or (iv) a portion of the organ within a subject during a plurality of respiratory cycles;

acquiring magnetic resonance (MR) data from the subject, wherein the MR data comprises a plurality of sets of imaging lines and a plurality of sets of SG lines, each of the plurality of sets of SG lines including at least a first SG line and a second SG line, and wherein (a) each respective set of imaging lines of the plurality of imaging lines is preceded by a respective one of the plurality of sets of SG lines that serve as a motion stamp for the respective set of imaging lines of the plurality of sets of imaging lines that the respective one of the plurality of sets of SG lines precede, and (b) a Fourier Transform of the SG lines is sensitive to respiratory-induced motion in a specific direction of the tumor, the portion of the tumor, the organ, or the portion of the organ;

taking the Fourier Transform of only the second SG line of each of the plurality of sets of SG lines to form a multi-channel projection profile time series;

deriving a respiratory curve comprising a plurality of time points by performing a principal component analysis (PCA) on the multi-channel projection profile time series and identifying an appropriate component of the multi-channel projection profile series that has a major Fourier mode matching a typical respiratory frequency, wherein each time point on the respiratory curve corresponds to the second SG line of each respective one of the plurality of sets of SG lines and provides an index for a position of the respective set of imaging lines following each respective one of the plurality of sets of SG lines along the specific direction;

applying band-pass filtering and peak detection to the respiratory curve to identify a plurality of respiratory cycles of the respiratory curve;

discarding any of the plurality of respiratory cycles having an abnormal duration or an outlier end-expiratory location;

sorting each remaining cycle of the plurality of respiratory cycles into a plurality of respiratory phases, based on the relative temporal locations or relative spatial positions indicated by the second SG line of the respective one of the plurality of sets of SG lines preceding each of the plurality of sets of imaging lines within the plurality of respiratory cycles; and reconstructing an image for at least a first respiratory phase of the plurality of respiratory phases and a second respiratory phase of the plurality of respiratory phases by applying a conjugate gradient (CG) sensitivity encoding (SENSE) scheme with self-sensitivity calibration, thereby producing at least two images that collectively depict motion of the tumor and/or non-tumor tissue.

2. The method of claim 1, wherein the 3D radial sampling k-space is filled by utilizing 2D golden means ordering.

3. The method of claim 1, wherein the first SG line and the second SG line that precede each of the plurality of sets of imaging lines are both superior-inferior (SI) readout lines.

4. The method of claim 3, wherein each of the plurality of sets of imaging lines comprises a number of imaging lines depending on a desired temporal resolution.

5. The method of claim 3, wherein the Fourier Transform of the second SG line of each of the plurality of sets of SG lines is sensitive to respiratory organ motion in an SI direction.

6. The method of claim 5, wherein each time point on the respiratory curve provides an index for the SI position of the respective set of imaging lines following each respective one of the plurality of sets of SG lines.

7. The method of claim 6, wherein peaks of the respiratory curve correspond to end-expiration.

8. The method of claim 1, wherein the subject is breathing irregularly or deeply.

9. The method of claim 1, wherein the tumor is a cancerous tumor.

10. The method of claim 1, wherein each of the plurality of sets of imaging lines includes at least one imaging line that extends along three dimensions in k-space.

11. The method of claim 1, wherein the first SG line and the second SG line of each of the plurality of sets of SG lines are identical to each other.

12. A magnetic resonance imaging system, comprising:
a magnet operable to provide a magnetic field;
a transmitter operable to transmit to a region within the magnetic field;
a receiver operable to receive a magnetic resonance signal from the region;
a processor operable to control the transmitter and the receiver; and
a non-transitory machine readable medium with instructions embedded thereon that when executed by the processor or a computing machine capable of communicating electronically with the processor cause the processor to direct the transmitter and receiver to execute a sequence, comprising:
applying a spoiled gradient echo sequence with a three-dimensional (3D) radial sampling k-space trajectory and one-dimensional (1D) projection-based self-gating (SG) to a volume of interest (VOI) comprising (i) a tumor, (ii) a portion of the tumor, (iii) an organ, or (iv) a portion of the organ within a subject during a plurality of respiratory cycles;
acquiring magnetic resonance (MR) data from the subject, wherein the magnetic resonance data comprises a plurality of sets of imaging lines and a plurality of sets of SG lines, each of the plurality of sets of SG lines including at least first SG line and a second SG line, and wherein (i) each respective set of imaging lines of the plurality of imaging lines is preceded by a respective one of the plurality of sets of SG lines that serve as a motion stamp for the respective set of imaging lines of the plurality of imaging lines that the respective one of the plurality of sets of SG lines precede, and (ii) a Fourier Transform of the SG lines is sensitive to respiratory-induced motion in a specific direction of the tumor, the portion of the tumor, the organ, or the portion of the organ;
taking the Fourier Transform of only the second SG line of each of the plurality of sets of SG lines to form a multi-channel projection profile time series;
deriving a respiratory curve comprising a plurality of time points by performing a principal component analysis (PCA) on the multi-channel projection profile time series and identifying an appropriate component of the multi-channel projection profile series that has a major Fourier mode matching a typical respiratory frequency, wherein each time point on the respiratory curve corresponds to the second SG line of each respective one of the plurality of sets of SG lines and provides an index for a position of the respective set of imaging lines following each respective one of the plurality of sets of SG lines along the specific direction;
applying band-pass filtering and peak detection to the respiratory curve to identify a plurality of respiratory cycles of the respiratory curve;
discarding any of the plurality of respiratory cycles having an abnormal duration or an outlier end-expiratory location;
sorting each remaining cycle of the plurality of respiratory cycles into a plurality of respiratory phases, based on the relative temporal locations or relative spatial positions indicated by the second SG line of the respective one of the plurality of sets of SG lines preceding each of the plurality of sets of imaging lines within the plurality of respiratory cycles; and
reconstructing an image for at least a first respiratory phase of the plurality of phases and a second respiratory phase of the plurality of respiratory phases by applying a conjugate gradient (CG) sensitivity encoding scheme with self-sensitivity calibration, thereby producing at least two images that collectively depict motion of the tumor and/or non-tumor tissue.

13. The magnetic resonance imaging system of claim 12, wherein the first SG line and the second SG line of each of the plurality of sets of SG lines are identical to each other.

14. A non-transitory machine-readable medium having machine executable instructions for causing one or more processors of a magnetic resonance imaging (MRI) machine and/or a computing machine capable of electronic communication therewith to execute a method, comprising:
utilizing an MRI machine to apply a spoiled gradient echo sequence with a three-dimensional (3D) radial sampling k-space trajectory and one-dimensional (1D) projection-based self-gating (SG) to a volume of interest (VOI) comprising (i) a tumor, (ii) a portion of the tumor, (iii) an organ, or (iv) a portion of the organ within a subject during a plurality of respiratory cycles;
acquiring magnetic resonance (MR) data from the subject, wherein the MR data comprises a plurality of sets of imaging lines and a plurality of sets of SG lines, each of the plurality of sets of SG lines including at least a first SG line and a second SG line, and wherein (a) each respective set of imaging lines of the plurality of imaging lines is preceded by a respective one of the plurality of sets of SG lines that serve as a motion stamp for the respective set of imaging lines of the plurality of sets of imaging lines that the respective one of the plurality of sets of SG lines precede, and (b) a Fourier Transform of the SG lines is sensitive to respiratory-induced motion in a specific direction of the tumor, the portion of the tumor, the organ, or the portion of the organ;

taking the Fourier Transform of only the second SG line of each of the plurality of sets of SG lines to form a multi-channel projection profile time series;

deriving a respiratory curve comprising a plurality of time points by performing a principal component analysis (PCA) on the multi-channel projection profile time series and identifying an appropriate component of the multi-channel projection profile series that has a major Fourier mode matching a typical respiratory frequency, wherein each time point on the respiratory curve corresponds to the second SG line of each respective one of the plurality of sets of SG lines and provides an index for a position of the respective set of imaging lines following each respective one of the plurality of sets of SG lines along the specific direction;

applying band-pass filtering and peak detection to the respiratory curve to identify a plurality of respiratory cycles of the respiratory curve;

discarding any of the plurality of respiratory cycles having an abnormal duration or an outlier end-expiratory location;

sorting each remaining cycle of the plurality of respiratory cycles into a plurality of respiratory phases, based on the relative temporal locations or relative spatial positions indicated by the second SG line of the respective one of the plurality of sets of SG lines preceding each of the plurality of sets of imaging lines within the plurality of respiratory cycles; and reconstructing an image for at least a first respiratory phase of the plurality of respiratory phases and a second respiratory phase of the plurality of respiratory phases by applying a conjugate gradient (CG) sensitivity encoding scheme with self-sensitivity calibration, thereby producing at least two images that collectively depict motion of the tumor and/or non-tumor tissue.

15. The non-transitory machine-readable medium of claim 14, wherein the tumor is a cancerous tumor.

16. The non-transitory machine-readable medium of claim 14, wherein the first SG line and the second SG line of each of the plurality of sets of SG lines are identical to each other.

* * * * *